United States Patent
Rissman et al.

(10) Patent No.: US 9,555,032 B2
(45) Date of Patent: Jan. 31, 2017

(54) METHODS FOR TREATMENT AND PREVENTION OF TAUOPATHIES AND AMYLOID BETA AMYLOIDOSIS BY MODULATING CRF RECEPTOR SIGNALING

(75) Inventors: Robert A. Rissman, San Diego, CA (US); Kuo-Fen Lee, Del Mar, CA (US); Wylie W. Vale, La Jolla, CA (US); Paul E. Sawchenko, Carlsbad, CA (US)

(73) Assignee: Research Development Foundation, Carson City, NV (US)

( * ) Notice: Subject to any disclaimer, the term of this patent is extended or adjusted under 35 U.S.C. 154(b) by 1804 days.

(21) Appl. No.: 12/663,805

(22) PCT Filed: Jun. 13, 2008

(86) PCT No.: PCT/US2008/066848
§ 371 (c)(1),
(2), (4) Date: Jun. 1, 2010

(87) PCT Pub. No.: WO2008/157302
PCT Pub. Date: Dec. 24, 2008

(65) Prior Publication Data
US 2010/0278743 A1    Nov. 4, 2010

Related U.S. Application Data

(60) Provisional application No. 60/943,672, filed on Jun. 13, 2007.

(51) Int. Cl.
*A61K 31/519* (2006.01)
*A61K 45/06* (2006.01)
*A61K 38/22* (2006.01)
*G01N 33/68* (2006.01)

(52) U.S. Cl.
CPC ......... *A61K 31/519* (2013.01); *A61K 38/2228* (2013.01); *A61K 45/06* (2013.01); *G01N 33/6896* (2013.01); *G01N 2500/00* (2013.01); *G01N 2800/2814* (2013.01); *G01N 2800/2821* (2013.01)

(58) Field of Classification Search
CPC  A61K 49/00; A61K 49/0004; A61K 49/0008; A61K 38/00; A61K 38/02; A61K 2123/00; A61K 2121/00; G01N 33/5088
USPC .............. 424/1.11, 1.49, 1.65, 1.69, 9.1, 9.2, 9.3,424/9.4, 9.5, 9.6, 9.7, 9.8; 514/1, 1.1; 530/300
See application file for complete search history.

(56) References Cited

U.S. PATENT DOCUMENTS

| | | | |
|---|---|---|---|
| 4,605,642 A * | 8/1986 | Rivier et al. ................. | 514/10.8 |
| 5,723,608 A * | 3/1998 | Yuan ............................ | 544/118 |
| 5,959,109 A * | 9/1999 | Whitten et al. ............... | 544/311 |
| 6,147,275 A | 11/2000 | Vale et al. ....................... | 800/18 |
| 6,187,781 B1 * | 2/2001 | Nakazato et al. ............. | 514/275 |
| 6,342,503 B1 * | 1/2002 | Aldrich et al. ................ | 514/272 |
| 6,353,152 B1 | 3/2002 | Lee et al. ......................... | 800/18 |
| 6,765,008 B1 * | 7/2004 | Chen ........................... | 514/265.1 |
| 6,838,274 B2 | 1/2005 | Vale, Jr. et al. ............ | 435/252.3 |
| 6,953,838 B2 | 10/2005 | Vale, Jr. et al. ............... | 530/350 |
| 7,087,617 B2 | 8/2006 | Corbett et al. ................. | 514/275 |
| 7,125,990 B2 | 10/2006 | Han et al. ...................... | 544/126 |
| 2002/0052387 A1 * | 5/2002 | Hodgetts .............. | C07D 239/36 514/269 |
| 2003/0186867 A1 * | 10/2003 | Facci et al. ...................... | 514/12 |
| 2005/0085479 A1 * | 4/2005 | Arneric ................ | A61K 31/415 514/247 |
| 2005/0101613 A1 * | 5/2005 | Corbett ................ | C07D 239/42 514/256 |
| 2005/0181460 A1 * | 8/2005 | Ohno ..................... | C07K 16/18 435/7.2 |
| 2013/0164743 A1 * | 6/2013 | Gozes ................ | G01N 33/6896 435/6.11 |
| 2015/0307626 A1 * | 10/2015 | Van Vlasselaer ...... | C07K 16/40 424/135.1 |

FOREIGN PATENT DOCUMENTS

| | | |
|---|---|---|
| EP | 0 729 758 | 9/1996 |
| EP | 1 908 764 | 4/2008 |
| WO | WO 98/03510 | 1/1998 |
| WO | WO 02/05749 | 1/2002 |

OTHER PUBLICATIONS

Baumann, Department of Neurology, University Hospital Zurich, Frauenklinikstrasse 26, 8091 Zurich (Apr. 23, 2012), Slides 1-82.*
Herholz, 2003, Annals of Nuclear Medicine, vol. 17, No. 2, pp. 79-89.*
The Alzheimer's Society, What is fronto-temporal dementia (including Pick's disease), alzheimers.org.uk (pp. 1-4, date unknown).*
Sjogren et al, 2000, Journal of Neural Transmission, vol. 107, pp. 563-579.*
Schulz et al, Proc. Natl. Acad. Sci., USA, 1996, vol. 93, pp. 10477-10482.*
Goedert et al, Proc. Natl. Acad. Sci., USA, 1993, vol. 90, pp. 5066-5070.*
Tao et al, Neuropsychopharmacology, 2006, vol. 31, pp. 2600-2609.*
Chen et al, J. Med. Chem., 1997, vol. 40, pp. 1749-1754.*
Schulz et al, Proc. Natl. Acad. Sci, USA, 1996, vol. 93, pp. 10477-10482.*

(Continued)

*Primary Examiner* — Adam M Weidner
(74) *Attorney, Agent, or Firm* — Parker Highlander PLLC

(57) ABSTRACT

Methods for treating or preventing tauopathies and/or Aβ amyloidosis by modulating CRF receptor signaling. Accumulation of hyperphosphorlyated tau protein in the CNS may be reduced by administration of CRF-R1 selective antagonists and/or CRF-R2 selective agonists. For example, in some aspects, methods for preventing the onset of Alzheimer's disease by administration of CRF-R1 selective antagonist are provided.

5 Claims, 14 Drawing Sheets

(56) References Cited

OTHER PUBLICATIONS

Buee et al, Brain Research Reviews, 2000, vol. 33, pp. 95-130.*
Gong et al, J. Biological Chemistry, 2000, vol. 275, No. 8, pp. 5535-5544.*
Johnson et al , J. Cell Science, 2004, 117, No. 24, pp. 5721-5729.*
Stoothoff et al, Biophysica Acta, 2005, vol. 1739, pp. 280-297.*
Dermaut 2004 "A novel presenilin 1 mutaiton associated with pick's disease but not .beta.-amyloid plaques" Ann Neurol 55:617-626.*
Fernandez-Nogales 2014 "Huntington's disease is a four-repeat tauopathy with tau nuclear rods" nature medicine 20(8):881-887.*
Honig 2003 "Stroke and the risk of Alzheimer's disease" Arch Neurol 60:1707-1713.*
Martinez 2002 "Differential actions of peripheral corticotropin-releasing factor (CRF), urocortin II, and Urocortin III on gastric emptying and colonic transit in mice: role of CRF receptor subtypes 1 and 2" Am Soc Pharma Exp Thera 301(2):661-617.*
Vitali 2004 "Soluble amyloid beta-protein is increased in frontotemporal dementia with tau gene mutations" J Alz Dis 6(1):45-51 (abstract only).*
Wilson 2003 "Proneness to psychological distress is associated with risk of alzheimer's disease" neurology 61:1479-1485.*
Kelly and Wilson 2004 "Proness to psychological distress is associated with risk of Alzheimer's disease: Response" Neurology 63(5):941.*
Baharians and Schonthal, "Autoregulation of protein phosphatase type 2A expression," J. Biol. Chem., 273:19019-19024, 1998.
Bale and Vale, "CRF and CRF receptors: role in stress responsivity and other behaviors," Annu. Rev. Pharmacol. Toxicol., 44:525-557, 2004.
Bale and Vale. "Increased depression-like behaviors in corticotropin-releasing factor receptor-2-deficient mice: sexually dichotomous responses," J. Neurosci., 23:5295-5301, 2003.
Bale et al., "Mice deficient for corticotropin-releasing hormone receptor-2 display anxiety-like behaviour and are hypersensitive to stress," Nat. Genet., 24:410-414, 2000.
Bayatti and Behl, "The neuroprotective actions of corticotropin releasing hormone," Ageing Res. Rev., 4:258-270, 2005.
Bayatti et al., "Brain region-specific neuroprotective action and signaling of corticotropin-releasing hormone in primary neurons," Endocrinology, 144(9):4051-60, 2003.
Behan et al., "Corticotropin-releasing factor (CRF), CRF-binding protein (CRF-BP), and CRF/CRF-BP complex in Alzheimer's disease and control postmortem human brain," J. Neurochem., 68(5):2053-60, 1997.
Behan et al., "Displacement of corticotropin releasing factor from its binding protein as a possible treatment for Alzheimer's disease," Nature, 378:284-7, 1995.
Blennow et al., "CSF total tau, Abeta42 and phosphorylated tau protein as biomarkers for Alzheimer's disease," Molecular Neurobiology, 24(1-3):87-97, 2001.
Chadwick et al., Corticotropin-Releasing Factor, Ciba Foundation Symposium, Chichester (Ed.), NY, Wiley, 357 pp., 1993.
Chen & Grigoriadis, "NBT 30775 (R121919), an orally active antagonist of the corticotropin-releasing factor (CRF) type-1 receptor for the treatment of anxiety and depression," Drug Dev. Res., 65(4):216-226, 2005.
Coste et al., "Abnormal adaptations to stress and impaired cardiovascular function in mice lacking corticotropin-releasing hormone receptor-2," Nat. Genet., 24:403-409, 2000.
Davis et al., "Neuropeptide abnormalities in patients with early Alzheimer disease," Arch. Gen. Psychiatry., 56(11):981-7, 1999.
De Souza et al., IREciprocal changes in corticotropin-releasing factor (CRF)-like immunoreactivity and CRF receptors in cerebral cortex of Alzheimer's disease, Nature, 310(6054):593-5, 1986.
Facci et al., "Corticotropin-releasing factor (CRF) and related peptides confer neuroprotection via type 1 CRF receptors," Neuropharmacology, 45(5):623-36, 2003.
Gotz et al., "A Decade of Tau Transgenic Animal Models and Beyond," International Society of Neuropathology and Brain Pathology, pp. 91-103, 2007.

Green et al., "Glucocorticoids increase amyloid-beta and tau pathology in a mouse model of Alzheimer's disease," J. Neurosci., 26:9047-9056, 2006.
Heinrichs et al., "Brain penetrance, receptor occupancy and antistress in vivo efficacy of a small molecule corticotropin releasing factor type 1 receptor selective antagonistBrain penetrance, receptor occupancy and antistress in vivo efficacy of a small molecule corticotropin releasing factor type I receptor selective antagonist," Neuropsychopharmacology, 27(2):194-202, 2002.
Horgan et al., "Longitudinal brain corticotropin releasing factor and somatostatin in a transgenic mouse (TG2576) model of Alzheimer's disease," J. Alzheimers Dis., 12(2):115-27, 2007.
International Preliminary Report on Patentability, issued in International Application No. PCT/US2008/066848, mailed Dec. 30, 2009.
International Search Report and Written Opinion, issued in International Application No. PCT/US2008/066848, mailed Jun. 22, 2009.
Iqbal et al., "Alzheimer paired helical filaments: bulk isolation, solubility, and protein composition," Acta Neuropathol. (Berl), 62:167-177, 1984.
Kang et al., "Acute stress increases interstitial fluid amyloid-beta via corticotropin-releasing factor and neuronal activity," Pro. Natl. Acad. Sci USA, 104(35):10673-8, 2007.
Keller et al., "Brain pharmacokinetics of a nonpeptidic corticotropin-releasing factor receptor antagonist," Drug Metab. Dispos., 30(2):173-176, 2002.
Kishimoto et al., "Deletion of crhr2 reveals an anxiolytic role for corticotropin-releasing hormone receptor-2," Nat. Genet., 24:415-419, 2000.
Li et al., "The pharmacology of DMP696 and DMP904, non-peptidergic CRF1 receptor antagonists," CNS Drug Rev., 11(1):21-52, 2005.
Mazur et al., "Sauvagine analogs selective for corticotropin releasing factor 2 receptor: effect of substitutions at positions 35 and 39 on CRF2R selectivity," Peptides, 26(5):887-891, 2005.
Misra et al., "Drug delivery to the central nervous system: a review," Journal of Pharmacy & Pharmaceutical Sciences: A Publication of the Canadian Society for Pharmaceutical Sciences, 6(2):252-273, 2003.
Office Communication, issued in European Patent Application No. 08 770 957.2, dated Jul. 29, 2010.
Pedersen et al., "Urocortin, but not urocortin II, protects cultured hippocampal neurons from oxidative and excitotoxic cell death via corticotropin-releasing hormone receptor type I," J. Neurosci., 22:404-412, 2002.
Phiel et al., "GSK-3alpha regulates production of Alzheimer's disease amyloid-Beta peptides," Nature, 423:435-439, 2003.
Pickhardt et al., "Screening for inhibitors of tau polymerization," Current Alzheimer's Research, 2(2):1567-2050, 2005.
Planel et al., "Alterations in glucose metabolism induce hypothermia leading to tau hyperphosphorylation through differential inhibition of kinase and phosphatase activities: implications for Alzheimer's disease," J. Neurosci., 24:2401-2411, 2004.
Planel et al., "Inhibition of protein phosphatase 2A overrides tau protein kinase I/glycogen synthase kinase 3 beta and cyclin-dependent kinase 5 inhibition and results in tau hyperphosphorylation in the hippocampus of starved mouse," J. Biol. Chem., 276:34298-34306, 2001.
Powers et al., "Immunohistochemical study of neurons containing corticotropin-releasing factor in Alzheimer's disease," Synapse, 1(5):405-10, 1987.
Rankin et al., "Tau phosphorylation by GSK-3Beta promotes tangle-like filament morphology," Molecular Neurodegeneration, 2:12, doi: 10.11861/1750-1326-2-12, 14 pages, 2007.
Rehman, "Role of CRH in the pathogenesis of dementia of Alzheimer's type and other dementias," Curr. Opin. Investig. Drugs, 3:1637-1642, 2002.
Rubenstein et al., "Paired helical filaments associated with Alzheimer disease are readily soluble structures," Brain Res., 372:80-88, 1986.

(56) References Cited

OTHER PUBLICATIONS

Sapolsky et al., "Prolonged glucocorticoid exposure reduces hippocampal neuron number: implications for aging," *J. Neurosci.*, 5:1222-1227, 1985.
Shaw et al., "Biomarkers of neurodegeneration for diagnosis and monitoring therapeutics," *Nature Reviews. Drug Discovery*, 6(4):295-303, 2007.
Smith et al., "Corticotropin releasing factor receptor 1-deficient mice display decreased anxiety, impaired stress response, and aberrant neuroendocrine development," *Neuron.*, 20:1093-1102, 1998.
Spires and Hyman, "Transgenic Models of Alzheimer's Disease: Learning from Animals," *The Journal of the American Society for Experimental NeuroTherapeutics*, 2:423-437, 2005.
Tache et al., "CRF1 receptor signaling pathways are involved in stress-related alterations of colonic function and viscerosensitivity: implications for irritable bowel syndrome," *British J. Pharm.*, 141:1321-1330, 2004.
Timpl et al., "Impaired stress response and reduced anxiety in mice lacking a functional corticotropin-releasing hormone receptor I," *Nat. Genet.*, 19:162-166, 1998.
Van Pett et al., "Distribution of mRNAs encoding CRF receptors in brain and pituitary of rat and mouse," *J. Comp. Neurol.*, 428:191-212, 2000.
Wallin et al., "CSF biomarkers for Alzheimer's disease: Levels of [beta]-amyloid, tau, phosphorylated tau relate to clinical symptoms and survival," *Dementia and Geriatric Cognitive Disorders*, 21(3):131-138, 2006.
Whitehouse et al., "Reductions in corticotropin releasing factor-like immunoreactivity in cerebral cortex in Alzheimer's disease, Parkinson's disease, and progressive supranuclear palsy," *Neurology*, 37(6):905-9, 1987.
Wilson, et al., "Chronic distress and incidence of mild cognitive impairment," *Neurology*, 68(24):2085-92, 2007.
Carroll et al., "Chronic stress exacerbates tau pathology, neurodegeneration, and cognitive performance through a corticotropin-releasing factor receptor-dependent mechanism in a transgenic mouse model of tauopathy," *The Journal of Neuroscience*, 31(40):14436-14449, 2011.
Isfort et al., "Discovery of corticotropin releasing factor 2 receptor selective sauvagine analogues for treatment of skeletal muscle atrophy," *Journal of Medicinal Chemistry*, 48(1):262-265, 2005.
Kehne and De Lombaert, "Non-peptidic $CRF_1$ receptor antagonists for the treatment of anxiety depression and stress disorders," *Current Drug Targets—CNS & Neurological Disorders*, 1:467-493, 2002.
McCarthy et al., "Recent advances with the $CRF_1$ receptor: design of small molecule inhibitors, receptor subtypes and clinical indications," *Current Pharmaceutical Design*, 5:289-315, 1999.
*Neuroendocrinology in Physiology and Medicine*, edited by Conn and Freeman, Humana Press, Chapter 15, p. 265, 2000.
Rissman et al., "Corticotropin-releasing factor receptor-dependent effects of repeated stress on tau phosphorylation, solubility, and aggregation," *PNAS*, 109(16):6277-6282, 2012.
Yoshiyama et al., "Synapse loss and microglial activation precede tangles in a P301S tauopathy mouse model," *Neuron*, 53:337-351, 2007.
Zorrilla and Koob, "Progress in corticotropin-releasing factor-1 antagonist development," *Drug Discov Today*, 15(9-10):371-383, 2010.
Chen et al., "Modulation of dendritic differentiation by corticotropin-releasing factor in the developing hippocampus," *PNAS*, 101(44):15782-15787, 2004.
Choi et al., "Corticotropin-releasing factor (CRF) and urocortin promote the survival of cultured cerebellar GABergic neurons through the type 1 CRF receptor," *J Korean Med Sci*, 21:518-526, 2006.
Fox et al., "Neuroprotection by corticotropin releasing factor during hypoxia in rat brain," *Stroke*, 24:1072-1076, 1993.
Koutmani et al., "Corticotropin-releasing hormone exerts direct effects on neuronal progenitor cells: implications for neuroprotection," *Molecular Psychiatry*, 18:300-307, 2013.
Lezoualc'h et al., "Corticotropin-releasing hormone-mediated neuroprotection against oxidative stress is associated with the increased release of non-amyloidogenic amyloid β precursor protein and with the suppression of nuclear factor-κβ," *Molecular Endocrinology*, 14(1):147-159, 2000.

\* cited by examiner

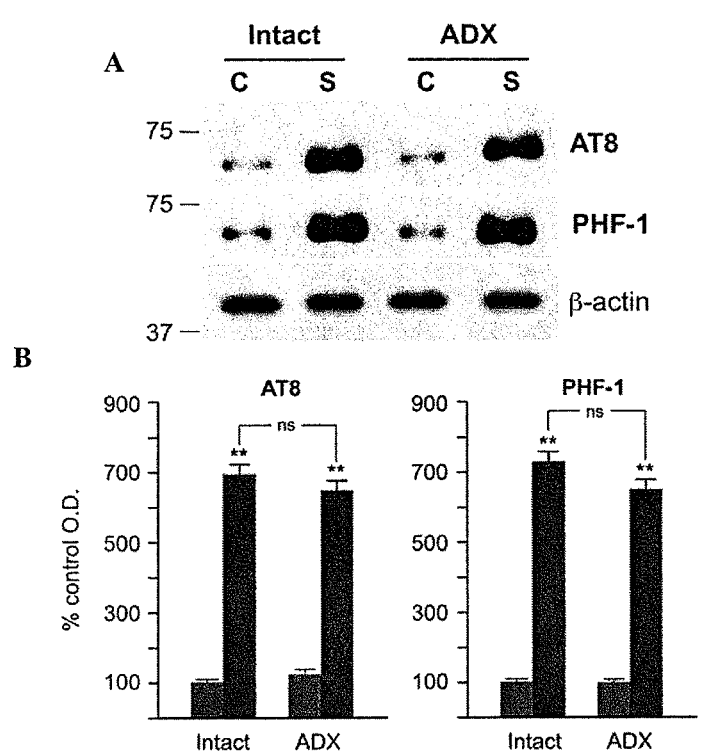
FIG. 2A-B

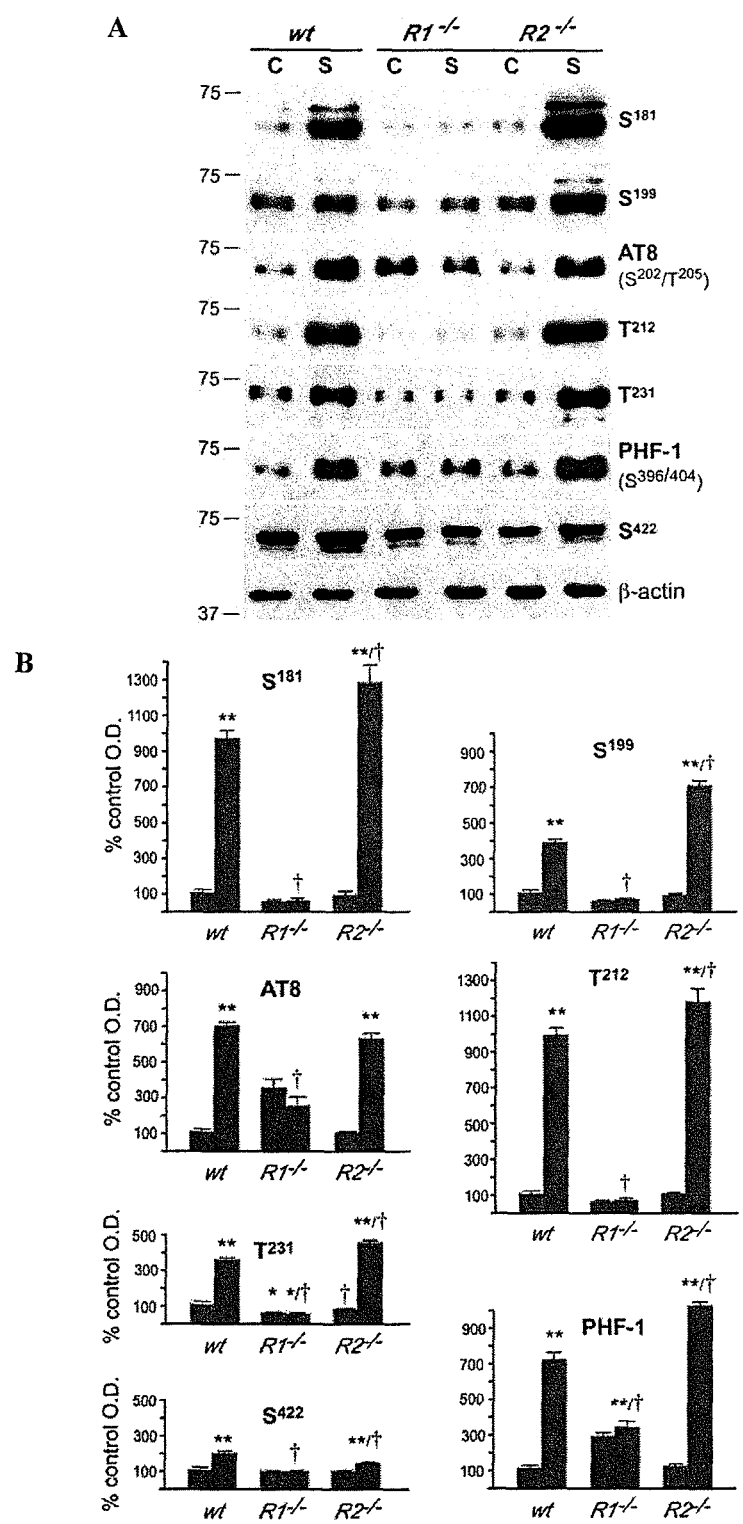
FIG. 3A-B

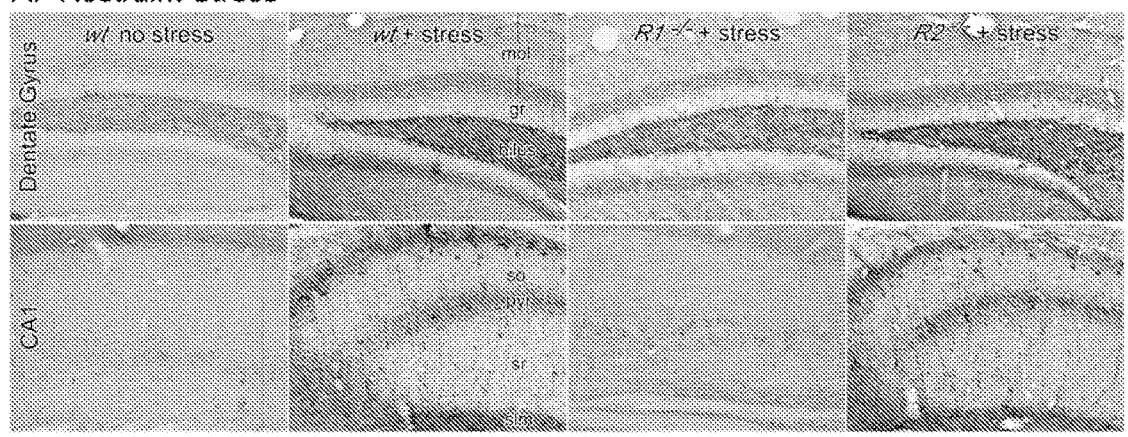
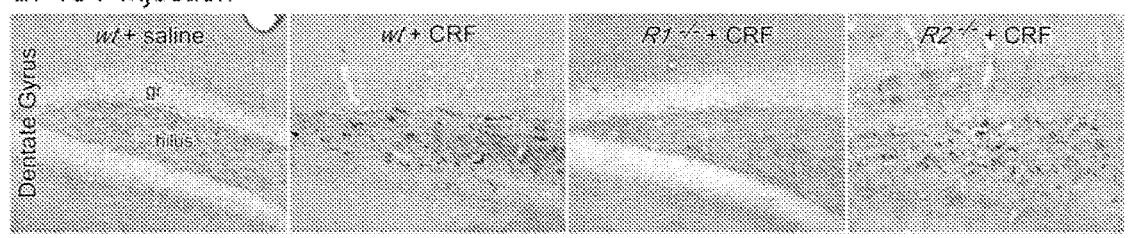
FIG. 4A-B

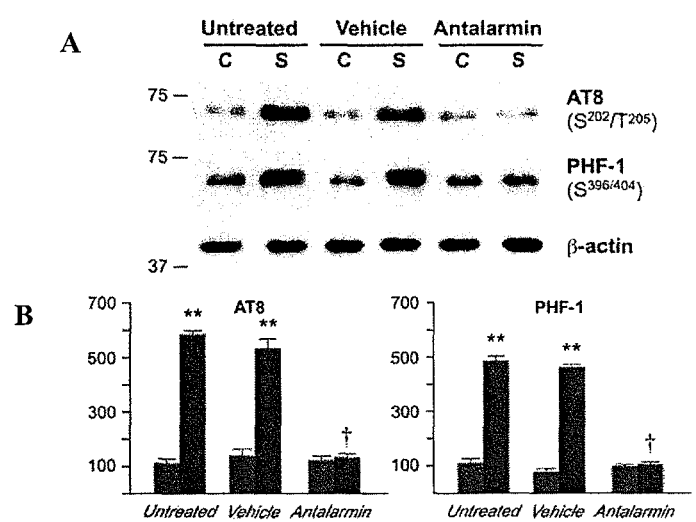
FIG. 5A-B

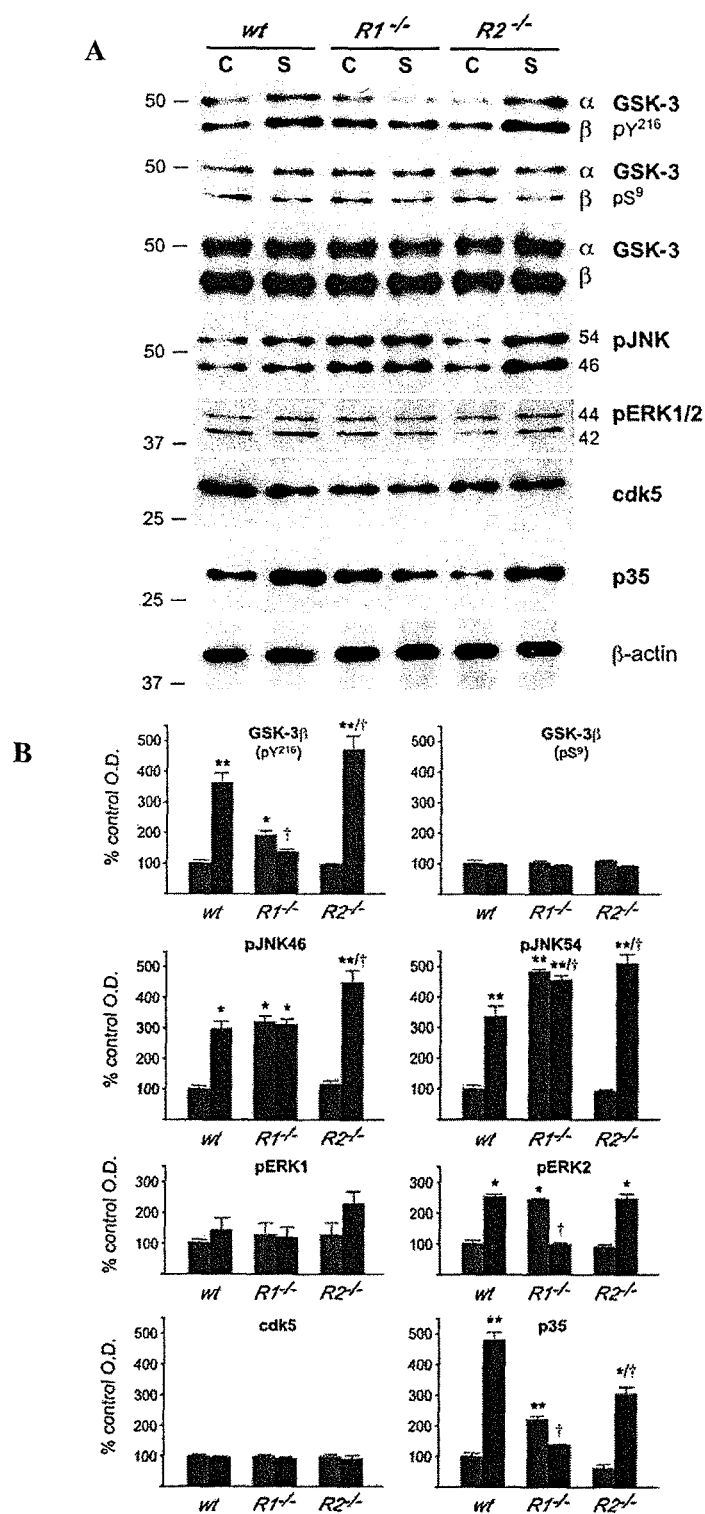
FIG. 6A-B

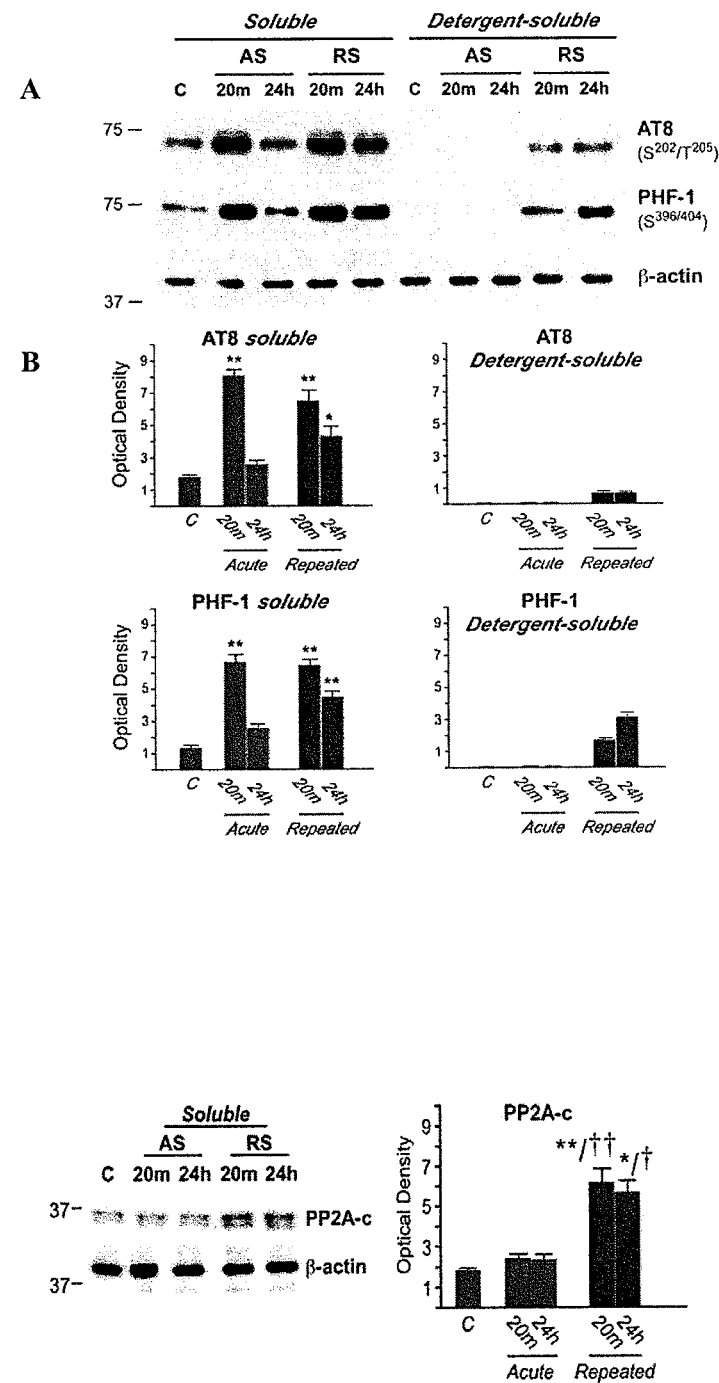
FIG. 7A-C

FIG. 9 A-B

A. Acute and Repeated Stress: Genotype
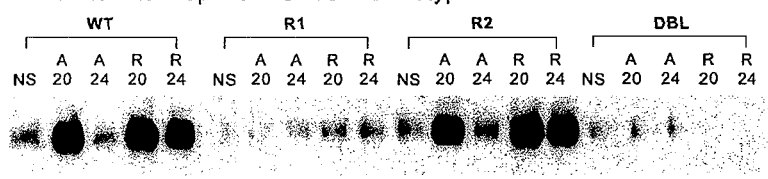
B. Repeated Stress and Tau Solubility
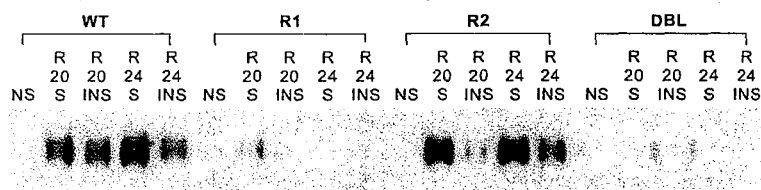
FIG. 12A-B

```
SEQUENCE LISTING

<160> NUMBER OF SEQ ID NOS: 4

<210> SEQ ID NO 1
<211> LENGTH: 38
<212> TYPE: PRT
<213> ORGANISM: Homo sapiens

<400> SEQUENCE: 1

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 2
<211> LENGTH: 38
<212> TYPE: PRT
<213> ORGANISM: Mus musculus

<400> SEQUENCE: 2

Phe Thr Leu Ser Leu Asp Val Pro Thr Asn Ile Met Asn Ile Leu Phe
1               5                   10                  15

Asn Ile Asp Lys Ala Lys Asn Leu Arg Ala Lys Ala Ala Ala Asn Ala
            20                  25                  30

Gln Leu Met Ala Gln Ile
        35

<210> SEQ ID NO 3
<211> LENGTH: 38
<212> TYPE: PRT
<213> ORGANISM: Homo sapiens

<400> SEQUENCE: 3

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
```

-continued

```
                  20                  25                  30

Arg Ile Leu Ala Arg Val
            35

<210> SEQ ID NO 4
<211> LENGTH: 38
<212> TYPE: PRT
<213> ORGANISM: Mus musculus

<400> SEQUENCE: 4

Val Ile Leu Ser Leu Asp Val Pro Ile Gly Leu Leu Arg Ile Leu Leu
1               5                   10                  15

Glu Gln Ala Arg Tyr Lys Ala Ala Arg Asn Gln Ala Ala Thr Asn Ala
            20                  25                  30

Gln Ile Leu Ala His Val
            35
```

METHODS FOR TREATMENT AND PREVENTION OF TAUOPATHIES AND AMYLOID BETA AMYLOIDOSIS BY MODULATING CRF RECEPTOR SIGNALING

This application is a national phase application under 35 U.S.C. §371 of International Application No. PCT/US2008/066848 filed Jun. 13, 2008 which claims priority to U.S. Application No. 60/943,672 filed on Jun. 13, 2007, the entire contents and disclosures of which are specifically incorporated by reference herein without disclaimer.

This invention was made with government support under grant number DK026741 awarded by the United States National Institutes of Health. The government has certain rights in the invention.

BACKGROUND OF THE INVENTION

1. Field of the Invention

The invention generally concerns protein mediated neurological disorders. In particular, the invention provides new methods to delay the onset and/or progression of tauopathies.

2. Description of Related Art

A wide variety of neurodegenerative disorders involve accumulation of insoluble tau protein. These disorders are collectively known as tauopathies due to the presence of tau tangles though, their clinical manifestation vary widely. One well-known tauopathy, Alzheimer's disease (AD) is defined neuropathologically by the accumulation of beta-amyloid plaques and neurofibrillary tangles (NFT) containing tau protein. NFTs in AD have been found to consist of hyperphosphorylated forms of the tau protein. Hyperphosphorylated tau exhibits reduced ability to bind and stabilize microtubules and can self-aggregate to form insoluble paired helical filaments (PHFs), which comprise NFTs (Gustke et al., 1992; Bramblett et al., 1993; Alonso et al., 1996). The incidence of NFTs is positively correlated with cognitive deficit and neuronal loss in AD (Arriagada et al., 1992; Gomez-Isla et al., 1997), and the discovery that mutations in the tau gene underlie autosomal dominant forms of frontotemporal dementia suggests that pathological changes in tau can serve as a principal cause of neurodegeneration and cognitive impairment (Hutton et al., 1998; Poorkaj et al., 1998; Spillantini et al., 1998). In view of this, tau phosphorylation has been studies as a possible mediator of tauopathies.

Exposure to a range of environmental insults, or stresses, can activate tau kinases and induce tau phosphorylation (tau-P) in the rodent central nervous system (CNS) (e.g., Korneyev et al., 1995; Papasozomenos, 1996; Korneyev, 1998; Yanagisawa et al., 1999; Planel et al., 2001, 2004; Arendt et al., 2003; Feng et al., 2005). This effect has been reported consistently in the hippocampal formation, a key structure in learning and memory, and the initial site of tau pathology in AD (Braak and Braak, 1991). Although acute stress-induced tau-P is reversible, the mechanisms that govern this phenomenon are unknown, and it is not clear whether and how it may be manifest under chronic stress conditions. Addressing these questions may better define the elusive links between the stress axis and AD-related pathogenic processes, as increased exposure and/or sensitivity to stress in humans and rodent models confers increased risk of dementia and AD neuropathology (Wilson et al., 2003; Jeong et al., 2006).

Warranting consideration in this respect are glucocorticoids, dominant stress hormones whose elevated levels in aging have been linked to increased neuronal vulnerability in hippocampus (Sapolsky et al., 1985, 1986). However, acute stress-induced tau-P is reportedly unaffected in adrenalectomized mice (Korneyev et al., 1995), suggesting that glucocorticoid secretion may not be pivotally involved. Alternatively, the corticotropin-releasing factor (CRF) signaling system plays an essential role in initiating pituitary-adrenal responses to stress, and has been implicated as a transmitter/modulator in CNS systems that mediate complementary autonomic and behavioral adjustments, earning consideration as a general mediator/integrator of stress adaptations (Chadwick et al., 1993). CRF and related ligands (urocortins 1-3) exert their biological effects via two G-protein coupled receptors (CRF-R1, CRF-R2) that are differentially distributed in brain (Van Pett et al., 2000), and exert convergent effects on a range of stress-related endpoints (Bale and Vale, 2004). CRF-R ligands can confer neuroprotection, in vitro, by altering amyloid precursor protein (APP) processing and suppressing tau kinases, and reduced central CRF expression has been documented early in AD progression (Rehman, 2002; Bayatti and Behl, 2005). Furthermore, studies examining the effects of CRF-R signaling on apoptotic cell death in neurons indicated that CRF-R2 agonists had no effect on neuronal death while CRF-R1 agonist has a protective effect (Pedersen et al., 2002). These results lead many in the field to contemplate that CRF-R1 agonist might have use as therapeutics in AD (Pedersen et al., 2002; U.S. Publn. 20030186867). However, to date the precise role of CRF-R signaling in the development and progression of tauopathies has remained unclear.

SUMMARY OF THE INVENTION

In a first embodiment the instant invention provides a method for treating, preventing or delaying the onset (or progression) of a tauopathy in a subject. Thus, in certain preferred aspects, the invention provides methods for delaying the onset or progression of a tauopathy comprising administering to the subject an effective amount of a CRF-R1 selective antagonist and/or an effective amount of a CRF-R2 selective agonist. In further aspects, the composition may comprise administering an effective amount of a CRF-R1 selective antagonist and/or an effective amount of a CRF-R2 selective agonist to the subject separately and/or in a single formulation. Thus, in certain cases, method of the invention may involve administering an effective amount of a CRF-R1 antagonist and a CRF-R2 agonist. As used herein the term tauopathy refers to a neurodegenerative disease that involves the formation of pathology involving alterations in tau protein, such as neurofibrillary tangles (NFTs). Thus, in some cases, a tauopathy may be Alzheimer's disease (AD), Amyotrophic lateral sclerosis/parkinsonism-dementia complex, Argyrophilic grain dementia, Corticobasal degeneration, Creutzfeldt-Jakob disease, Dementia pugilistica, Diffuse neurofibrillary tangles with calcificationa, Down's syndrome, Frontotemporal dementia with parkinsonism (linked to chromosome 17), Gerstmann-Straussler-Scheinker disease, Hallervorden-Spatz disease, Myotonic dystrophy, Niemann-Pick disease (type C), Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy, Subacute sclerosing panencephalitis or Tangle only dementia. For instance, in certain aspects the invention provides methods and compositions for delaying the onset or progression of AD. However, in certain other aspects, methods for treating, delaying the onset or delaying the progression of a non-Alzheimer tauopathy are provided.

In further embodiments the invention provides a method for treating, blocking or delaying the onset and/or progression of an amyloid beta amyloidosis (Aβ amyloidosis) in a subject comprising administering to the subject a composition comprising an effective amount of a CRF-R1 selective antagonist and/or an effective amount of a CRF-R2 selective agonist. Thus, in some aspects, method of the invention may involve administering an effective amount of a CRF-R1 antagonist and a CRF-R2 agonist separately and/or in a single formulation. In further aspects, Aβ amyloidosis is a neurodegenerative disease that involves the formation of amyloid beta (Aβ) plaques. In still further aspects, the Aβ amyloidosis involves production of Aβ by truncation or cleavage processing of the amyloid precursor protein (APP). Thus, in some aspects, an Aβ amyloidosis may be AD, Cerebral amyloid angiopathy, Inclusion body myositis, or variants of Lewy body dementia. For instance, in certain aspects the invention provides methods and compositions for delaying the onset or progression of AD. However, in certain other aspects, methods for treating, delaying the onset or delaying the progression of a non-Alzheimer Aβ amyloidosis are provided.

In some embodiments the invention concerns administration of a composition (e.g., a CRF-R1 antagonist) to a subject. A subject may refer to any animal that is a recipient of the methods or compositions herein, though in a preferred embodiment, the subject is a human. The skilled artisan will recognize that in certain cases, the methods of the invention involve delaying or preventing the progression of a tauopathy and/or an Aβ amyloidosis in a subject. Thus, in certain aspects, a subject may be a subject that has been diagnosed with a tauopathy and/or an Aβ amyloidosis. For example, a subject may be defined as a person who has been diagnosed with AD or has clinical and/or pathological signs of AD. In still other embodiments, there is provided a method for preventing or delaying the onset of a tauopathy and/or an Aβ amyloidosis. Thus, the skilled artisan will recognize in some cases subjects are defined as not having a tauopathy and/or an Aβ amyloidosis. For example, in some aspects, a subject maybe at risk for developing a tauopathy and/or an Aβ amyloidosis. An at risk subject may for instance, have a genetic predisposition to a tauopathy and/or an Aβ amyloidosis (e.g., as ascertained by family history or a genetic mutation). In still further cases, an at risk subject may lack clinical disease but comprise risk factors for disease such as declining cognitive (e.g., mild cognitive impairment (MCI)) or memory function or elevated levels of a marker protein (e.g., tau or amyloid beta) in the serum or CNS or increased or advancing age.

Thus, in some preferred embodiments, there is provided a method for delaying the onset or progression of a tauopathy and/or an Aβ amyloidosis in a subject comprising administering an effective amount of a CRF-R1 selective antagonist. As used herein the phrase CRF-R1 selective antagonist means an antagonist that is more effective at antagonizing CRF-R1 signaling than CRF-R2. For example, in certain cases, a CRF-R1 selective antagonist has between about 10 and about 100, 1000, or 10,000 fold more antagonist activity on CRF-R1 than on CRF-R2. For example, a selective antagonist may be defined as molecules that binds to CRF-R1 with a 10, 100, 1000 or 10,000 fold higher affinity than it binds to CRF-R2. Thus, in some cases, a CRF-R1 selective antagonist has essentially no CRF-R2 antagonist activity as exemplified by antalarmin. In still other cases a CRF-R1 selective antagonist may comprise CRF-R2 agonist activity.

Furthermore, a CRF-R1 antagonist as described herein may also comprise molecules that reduced expression of CRF-R1 thereby antagonizing the CRF-R1 signaling pathway. For example, in certain aspects a CRF-R1 antagonist may be a CRF-R1 selective siRNA.

In still further embodiments there is provided a method for delaying the onset or progression of a tauopathy and/or an Aβ amyloidosis in a subject comprising administering an effective amount of a CRF-R2 selective agonist. As used herein the phrase CRF-R2 selective agonist refers to an agonist that is more effective at agonizing CRF-R2 than CRF-R1. For example, in certain cases, a CRF-R2 selective agonist has between about 10 and about 100, 1000, or 10,000 fold more agonist activity on CRF-R2 than CRF-R1. For example, a selective agonist may be defined a molecule that binds to CRF-R2 with about a 10, 100, 1000 or 10,000 fold higher affinity than it binds to CRF-R1. Thus, in some cases, a CRF-R2 selective agonist has essentially no CRF-R1 agonist activity. In still other cases, a CRF-R2 selective agonist comprises CRF-R1 antagonist activity. Furthermore, a CRF-R2 agonist as described herein may also comprise an indirect agonist such as molecules that increases expression of CRF-R2 thereby agonizing the CRF-R2 signaling pathway.

As described here, in certain aspects the invention concerns administering an effective amount of a CRF-R1 selective antagonist and/or a CRF-R2 selective agonist. The skilled artisan will readily understand that an important aspect of the invention is the selectivity of a particular agonist or antagonist. Thus, depending on the level of selectivity of a particular CRF-R agonist or antagonist the effective concentration for administration may vary. Furthermore, as described supra, an important marker for the effectiveness of a CRF-R agonist or antagonist is reduction of stress-induced tau phosphorylation or reduction of stress-induced insoluble tau protein accumulation or the formation of Aβ plaques. Nonetheless, transient tau phosphorylation may be an important mediator of stress response and thus complete abrogation of phosphorylation is not preferred. Hence, in some aspects, an effective dosage is defined a dosage that partially reduces stress-induced tau protein phosphorylation such as dosage that reduces tau phosphorylation by between about 90%, 80%, 70%, 60%, 50%, 40%, 30% or 20% and 10% following stress. In other aspects, an effective dosage is defined a dosage that reduce amyloidosis by between about 90%, 80%, 70%, 60%, 50%, 40%, 30% or 20% and 10%. Thus, in certain cases, the instant invention provides a method for determining an effective amount of a CRF-R1 antagonist or a CRF-R2 agonist dosage by assessing a reduction of stress-induced tau phosphorylation and/or a reduction in Aβ amyloidosis. For example, a CRF-R1 antagonist with essentially no CRF-R2 agonist activity such as antalarmin may be administered in a dosage equivalent to a murine dosage of between about 2 mg/kg and 200 mg/kg (e.g., about 6 to about 600 mg/m$^2$), such as a dose of about 20 mg/kg (e.g., about 60 mg/m$^2$).

Methods of administering a CRF-R1 antagonist or CRF-R2 agonist of the invention will depend upon the particular type of agonist or antagonist used. In general, a CRF-R1 selective antagonist or a CRF-R2 selective agonist may be administered by any method known in the art such as topically, intravenously, intradermally, intraarterially, intraperitoneally, intracranially, intrathecally, intracerebroventricularly, mucosally, intraocularally, subcutaneously or orally. In certain aspects, molecules or compositions with the ability to cross the blood-brain barrier (BBB) may be administered topically, intravenously, intradermally, intraarterially, intraperitoneally, mucosally, intraocularally, subcutaneously or orally. On the other hand, in some cases, molecules or compositions unable to traverse the BBB maybe administered directly to the CNS. In some very specific aspects, the molecules or compositions directly administered to the CNS can be administered intrathecally, intracerebroventricularly, or intracranially.

In some very specific aspects of the invention a CRF-R1 specific antagonist may comprise a peptide or polypeptide antagonist, such as a modified CRF ligand polypeptide. Furthermore, in certain aspects, a CRF-R1 selective antagonist may be a CRF-R1 binding antibody or a fragment thereof. In still other aspects of the invention a CRF-R1 selective antagonist comprises a small molecule antagonist. For example, a CRF-R1 antagonist may be TIMP, DMP696, DMP904, CRA 1000, CRA 1001, SSR125543A, SN003, DMP695, NBI 27914, NBI 30775, NBI 34041, NBI 35965, CP154,526, R121919, R121920, LWH234, antalarmin or a derivative thereof. In a highly preferred embodiment the CRF-R1 antagonist is a water-soluble antagonist that may be administered orally.

In still further specific aspects of the invention a CRF-R2 specific agonist for use according to the invention comprises a peptide or polypeptide CRF-R2 agonist. For example, a CRF-R2 peptide agonist may be a Ucn 2 or Ucn 3 peptide or a derivative thereof. A number of Ucn 2 and Ucn 3 derived peptides comprising selective CRF-R2 agonist activity have been developed and may be used according to the invention see for example U.S. Pat. Nos. 6,953,838 and 6,838,274 and Mazur et al. (2005). Furthermore, in certain aspects a CRF-R2 selective agonist may be a CRF-R2 binding antibody or a fragment thereof. In still further aspects of the invention, a CRF-R2 selective agonist for use according to the invention is a small molecule agonist.

In yet further embodiments of the invention a CRF-R1 selective antagonist and/or a CRF-R2 selective agonist may further comprises a CNS targeting agent. As used herein CNS targeting merely refers to an agent that increases the amount of a composition or molecule in the CNS. For example, in some aspects, a CNS targeting agent is a polypeptide such as an antibody or cationized albumin. Thus, polypeptide CNS targeting agents may in some aspects, be bound to a CRF-R agonist or antagonist for use according to the invention. In some very specific cases, a peptide (or polypeptide) CRF-R agonist or antagonist may be provided as a fusion protein with a CNS targeting polypeptide. For example, a CNS targeting polypeptide may be an antibody that mediates transcytosis across the BBB. Such an antibody may comprise, for example, a monoclonal antibody to transferrin receptor (e.g., OX26) or monoclonal antibodies to the insulin receptor (Schnyder & Huwyler, 2005). In certain other cases nanoparticles such as Polysorbate 80-coated polybutylcyanoacrylate nanoparticles may be used to deliver compositions to the CNS (Olivier, 2005). In still further aspects, CNS targeting polypeptides may be conjugated to liposomes to form CNS targeting complexes (Schnyder & Huwyler, 2005). Furthermore, peptide and polypeptide CRF-R1 antagonists and/or CRF-R2 agonists may be targeted to the CNS by glycosylation, for example as described in Egleton & Davis (2005).

In still further embodiments of the invention there is provided a method for identifying an agent for treating, preventing the onset or preventing progression of a tauopathy comprising: (a) administering a candidate agent to an animal; (b) subjecting the animal to a stress; (d) determining tau phosphorylation, dephosphorylation (e.g., PP2A-c, other tau phosphatase protein level, or tau kinase activity) or insoluble tau accumulation in the CNS following stress wherein a decreased in tau phosphorylation, a decrease in PP2A-c level or decreased insoluble tau accumulation in animals treated with a candidate agent relative to control animals is indicative of activity in treating, preventing the onset or preventing progression of a tauopathy. In certain aspects, methods of the invention may involve determining tau phosphorylation, PP2A-c level or insoluble tau accumulation in a hippocampal tissue following stress. Furthermore, in certain aspects, determining a decrease tau phosphorylation or insoluble tau protein may comprise measuring the amount of tau phosphorylation or a level of insoluble tau protein accumulation. In still further aspects a method may further comprise between steps (b) and (d), step (c): repeating steps (a) and (b) to determine the effect of a candidate agent during repeated/chronic stress. Thus, in some aspects steps (a) and (b) may be repeated 2, 3, 4, 5, 6, 7, 8, 9, 10, 20, 50, 100 times or more. In further aspects steps (a) and (b) comprise exposing animals to a series of chronic variable stress. The skilled artisan will recognize that in some aspects such a method may be used to determine an effective amount of a CRF-R1 antagonist or CRF-R2 agonist to reduce tau phosphorylation by between about 90%, 80%, 70%, 60%, 50%, 40%, 30% or 20% and 10% following stress.

In certain preferred aspects an animal for use according to the invention is a rat or a mouse. Various stress conditions maybe used in methods of the invention. For example, a stress may be a physical stress or, more preferably, an emotional stress. In certain preferred aspects a relatively mild stress, such as physical restraint stress is used. In still further cases, heat shock, forced swimming, starvation or exposure to anesthetics may be used to apply stress to animals.

Methods for determining tau phosphorylation, or tau phosphatase (PP2A-c) protein level or insoluble tau accumulation are well known in the art. For example, tau phosphorylation is by determined by biochemical, anatomical or antigen capture approaches such as binding of a phosphorylation specific antibody (e.g., in a Western blot, immunohistochemistry or ELISA). Likewise, in certain aspects, antibody binding may be used to determine PP2A-c protein level, for example after repeated stress. Methods for determining insoluble tau protein accumulation are also well known in the art. For example, insoluble tau protein may be determined by detergent extraction and detection by antibody binding. Furthermore, insoluble tau accumulation may be determined by detecting tau aggregates, filaments or tangles for example by microscopy (e.g., electron microscopy) or by scanning techniques such as Positron Emission Tomography (PET) scan or Magnetic Resonance Imaging (MRI).

Methods for determining Aβ plaques or Aβ peptide level are well known in the art. For example, Aβ plaques are detected by biochemical, anatomical or antigen capture approaches such as binding of a Aβ specific antibody (e.g., in a Western blot or ELISA). Likewise, in certain aspects, antibody binding may be used to determine Aβ peptide level, for example after repeated stress, chronic variable stress, or after CRF-R1 antagonist treatment.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

FIG. 2A-B: The role of glucocorticoids in stress-induced tau-P. FIG. 2A, Western analysis of hippocampal tau-P at the AT8 and PHF-1 sites under control (C) and acute stress (S) conditions in intact and adrenalectomized (ADX) mice. ADX mice were supplemented with corticosterone to approximate basal circulating steroid levels. FIG. 2B, Quantitative analysis, expressed as mean±SEM percentage of integrated intensity values of intact unstressed controls, reveals that intact and ADX animals manifest comparably robust stress-induced increments in tau-P at each site, whose magnitude did not differ significantly. Light bars and dark bars indicate unstressed and stressed animals respectively. **, indicates that results differ significantly from intact, unstressed controls, P<0.001; ns, non-significant (P>0.05). n=3 mice/condition. β-actin was used as a loading control.

FIG. 3A-B: Differential regulation of stress-induced tau-P by CRF-R status. FIG. 3A, phosphorylation responses of seven AD-relevant tau sites in hippocampal extracts from wild type (wt), CRF-R1−/− and CRF-R2−/− mice killed at 20 min after acute restraint stress (S) or no treatment (C). FIG. 3B, quantitative analysis revealed that wt animals displayed the expected increases in tau-P following stress at all epitopes. CRF-R1−/− animals displayed elevated basal levels of phosphorylation at the AT8 and PHF-1 sites, but did not manifest significantly increased responses following stress at any site. Conversely, CRF-R2−/− mice showed normal basal levels of tau-P at all sites, but exaggerated responses to stress at five of the seven epitopes assayed. Light bars and dark bars indicate unstressed and stressed animals respectively. Data are presented as mean±SEM percentage of wt control values. *, differs significantly from unstressed wt condition, P<0.01; **, P<0.001; †, differs from wt stressed group, P<0.05. n=3 mice/condition. β-actin was used as a loading control.

FIG. 4A-B: Cellular localization of stress- and peptide-induced tau-P. FIG. 4A, immunoperoxidase staining for PHF-1-immunoreactivity in the dentate gyrus (top) and CA1 field (bottom) of mouse hippocampus as a function of stress status and genotype. Phosphorylation is localized to distinct perikaryal/dendritic and axonal elements, and, importantly, varies with stress exposure and CRF-R status in a manner identical to that seen by Western analysis (FIG. 3). FIG. 4B, PHF-1 in the dentate gyrus of mice injected icv with synthetic CRF. Tau-P varied as a function of genotype in a similar fashion to that seen in stressed animals (FIG. 4A).

FIG. 5A-B: CRF-R1 antagonist blocks stress-induced tau-P. Western analysis (FIG. 5A) and quantitation (FIG. 5B) of tau-P at the AT8 and PHF-1 sites in hippocampal extracts from mice pretreated with vehicle or the small-molecule CRF-R1 antagonist, antalarmin (20 mg/kg, ip.), and subjected to acute stress or no further treatment, expressed as a percentage of levels in untreated controls (C). At each site, antagonist treatment did not affect basal levels of phosphorylation, but blocked the stress-induced increment. The vehicle used for drug administration had no significant effect under basal or stress conditions. Light bars and dark bars indicate unstressed and stressed animals respectively. **, differs significantly from unstressed controls, P<0.001; †, differs from untreated stressed group, P<0.05. n=3 per condition. β-actin was used as a loading control.

FIG. 6A-B: Modulation of tau kinase activity by stress and CRF-R status. Western analyses using phosphoepitope-specific antibodies to interrogate stress- and/or genotype-dependent variations in the activation state of glycogen synthase kinase-3 (GSK-3), c-jun N-terminal kinases (JNK46/54) and the extracellular signal-regulated kinases 1 and 2 (ERK1/2); relative levels of cyclin-dependent kinase 5 (cdk5) and its activator protein, p35, were also evaluated. The behavior of each kinase group recapitulates aspects of the general pattern of tau-P responses in the same design. Thus, the activated ($pY^{216}$) form of GSK-3β is upregulated by stress in wt mice, and this response is blocked CRF-R1-deficient animals and exaggerated in CRF-R2 mutants. The inhibitory ($pS^9$) form and total (unphosphorylated) GSK3 are unresponsive over these conditions. Both phospho-JNK isoforms were also stress-responsive, and more so in CRF-R2 knockouts; these kinases were distinguished by very high basal phosphorylation levels in CRF-R1−/− mice, which may relate to elevated tau-P observed in this condition at the AT8 site (see FIG. 3). Levels of phospho-ERKs, particularly ERK1, were relatively unresponsive. Levels of cdk5 were stable across the conditions in force here, but its p35 activator protein was strongly upregulated by stress in wt and CRF-R2−/− mice. Light bars and dark bars indicate unstressed and stressed animals respectively. Data are presented as mean SEM percent of unstressed wt values. *, differs significantly from wt control, P<0.01; **, P<0.001. †, differs significantly from wt stress condition, P<0.05. β-actin was used as a loading control.

FIG. 7A-C: FIG. 7A-B, repeated stress results in chronic elevations and reduced solubility of phosphorylated tau. Western analysis of hippocampal tau-P at the PHF-1 and AT8 sites of mice sacrificed 20 min or 24 hr after 30 min acute restraint or 14 consecutive daily exposures. Analysis was carried out on both soluble and detergent-soluble fractions. Under acute stress conditions tau-P is transient and contained wholly within the soluble fraction, whereas repeated stress results in elevated levels of tau-P at both time points, and the appearance of a significant portion of phospho-tau in the detergent-soluble fraction. These data suggest that the effects of repeated emotional stress on tau-P are cumulative, and associated with increased sequestration in the cellular fraction known to contain the bulk of PHFs in the AD brain. Note that for this analysis, data are expressed as mean±SEM optical density, rather than as a percentage of control values, to reflect that lack of detectable signal in detergent-soluble extracts under control conditions. *, differs significantly from control, $P<0.01$; **, $P<0.001$. β-actin was used as a loading control. FIG. 7C, acute and repeated stress effects on PP2A-c levels. Western analysis of relative levels of PP2A-c in mice sacrificed 20 min or 24 hr after 30 min acute restraint or 14 consecutive daily exposures. Under control and acute stress conditions, low levels of free PP2A-c subunit (~37 kDa) were found within soluble fractions (lanes 1-3). Under conditions of repeated stress, PP2A-c protein was elevated at both time points (lanes 4-5). No PP2A-c signal was observed in detergent-soluble fractions. These data implicate alterations in tau phosphatase activity as contributing to tau-P under repeated stress conditions, at least (cf FIG. 7). Data are expressed as mean±SEM optical density. *, differs significantly from control, $P<0.01$; **, $P<0.001$. †, differs significantly from acute 20 min stress condition, $P<0.01$; †† $P<0.001$. β-actin was used as a loading control.

FIG. 9A, Western blots showing relative levels of tau-P at the PHF-1 site in unstressed mice (NS) and at varying intervals after LPS injection (10 µg/kg, ip). A robust increment is seen, peaking at 60-90 min after injection. FIG. 9B, Western blots from individual WT and single or double CRFR knockout mice. Tau-P responses at the PHF-1 site are relatively consistent across genotypes, while those of CRFR2 and double mutants at the AT8 site are variable, and, on average, suppressed. This pattern of results contrasts sharply with those obtained in a restraint stress model, and suggests that that distinct circuitry and mechanisms underlie tau-P responses to emotional (restraint) and physiological (LPS) stressors.

FIG. 12A-B: CRFR-dependence and solubility of repeated stress-induced tau-P. Western blots detects tau-P at the PHF-1 site in wt, CRFR1 (R1), CRFR2 (R2) and double CRFR (DBL) knockout transgenic mice, which were sacrificed 20 min (20) or 24 hr (24) after acute (A) or repeated (R) restraint stress. Data from unstressed controls (NS) are shown for comparison. FIG. 12A, Genotype effects. Results in wt mice confirm that repeated stress results in persistent accumulations of phospho-tau (compare A24 and R24 lanes). All stress effects seen in wt mice are abolished in R1 and DBL knockouts, and tend to be exaggerated in R2 mutants. FIG. 12B, Solubility of phospho-tau as a function of stress and genotype. Hippocampal extracts from repeatedly stressed mice of each genotype and stress condition, separated into soluble (S) and insoluble (INS) fractions. Repeated, but not acute, stress results in accumulations of phospho-tau in insoluble cellular fractions. This effect is seen in wt and R2-deficient mice, where it tends to be accentuated (wt vs. R2 group comparison at R24/INS differs significantly, $P<0.01$), but not in R1 or DBL knockouts.

at this time point was significantly reduced by antagonist treatment in both stressed and unstressed mice, while stress alone had no significant effect. Thus, treatment with the CRFR1 antagonist blocked or delayed the development of amyloid pathology in this mouse AD model.

DETAILED DESCRIPTION OF THE INVENTION

Tauopathies are characterized by CNS accumulation of Tau protein aggregates know as tangles. Certain tauopathies also involve other protein aggregations, such as the CNS plaques comprised of amyloid beta protein that characterize Alzheimer's disease. Of all tauopathies Alzheimer's disease has received the greatest amount of attention by the medical research community. For example, many therapies have focused on reducing the neurological symptoms of Alzheimer's disease such as memory loss. Still other therapies, such as "Alzheimer's vaccines," that direct immune cells to degrade protein aggregates have also been proposed and are currently under evaluation. Finally, recent studies have suggested that therapeutics may be used to prevent toxicity of protein aggregates by preventing apoptosis in neurons. However, there remains a need for approaches for reducing accumulation or even initial aggregation tau protein to prevent clinical manifestation of tauopathies delay the clinical progression of such diseases.

Figure 8:
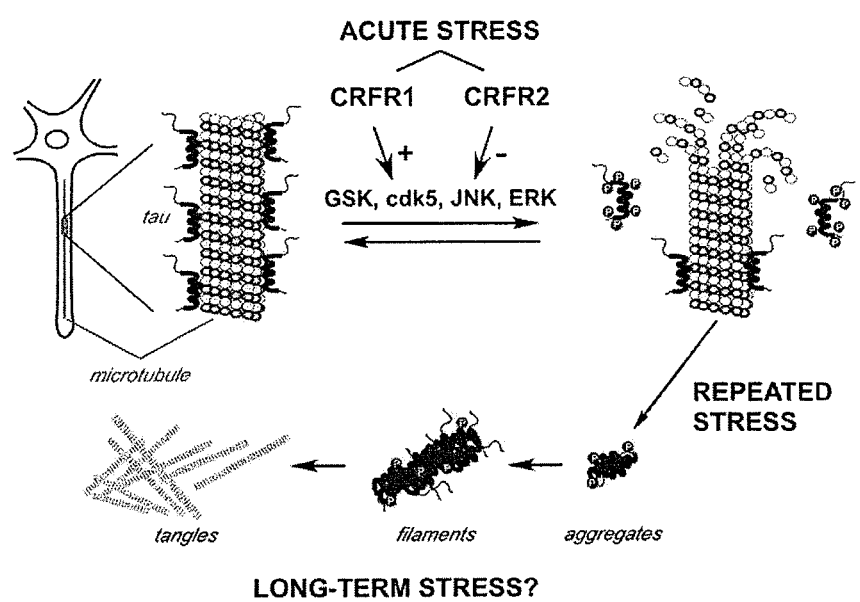
FIG. 8: CRF-R involvement in stress-induced tau phosphorylation. Schematic summary of the progression of events leading to neurofibrillary tangle formation in AD, adapted from (Drewes, 2004). Indicated upon this are the present findings supporting a differential involvement of CRF-Rs, acting via specific tau kinases, in mediating acute stress-induced tau-P (circles). While acute stress effects are transient and readily reversible, repeated stress exposure produces cumulative increases in phosphorylated tau, a portion of which is sequestered in detergent-soluble fractions. Long-term increases in stress exposure and/or sensitivity may result in development of paired helical filaments and tangles that represent a defining feature of AD neuropathology.
Figure 9:
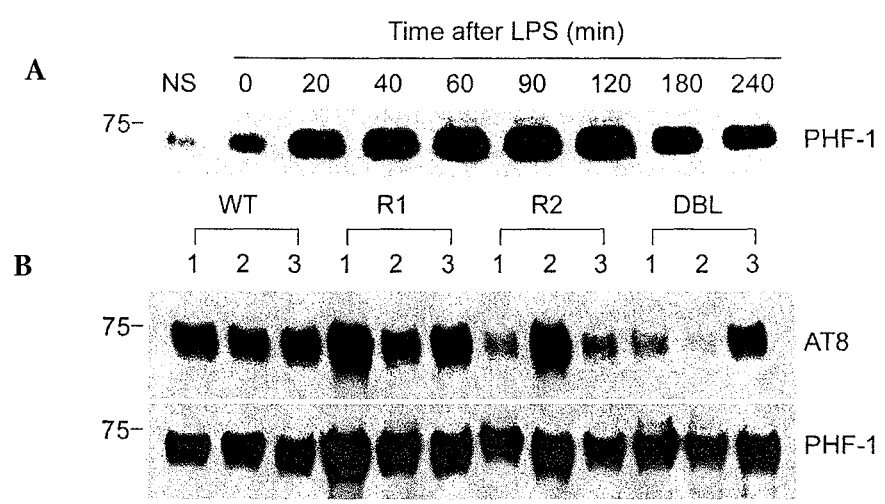
FIG. 9A-B: Time course and genotype dependence of acute immune challenge effects on hippocampal tau phosphorylation.

Studies herein extend the range of insults known to provoke tau phosphorylation to include a representative emotional stressor, and provide evidence bearing on its mechanism (FIG. 8). The abrogation of stress-induced tau-P in CRF-R1-deficient animals, and the enhancement observed in CRF-R2 mutants, were paralleled by altered activities of specific tau kinases. Furthermore, the demonstration that repeated stress exerts cumulative effects on tau-P, and results in sequestration of phospho-tau in insoluble forms suggests a possible mechanism for tau aggregate accumulation in tauopathies. Importantly, the role of CRF-R signaling in stress induced tau phosphorylation elucidated here indicated that CRF-R1 antagonists and CRF-R2 agonists may be used to reduce stress induced tau phosphorylation and resultant insoluble accumulation of tau. In support of this it was shown that a CRF-R1 selective antagonist can reduce stress induced tau phosphorylation in the brains of test animals (FIG. 5A-B). Thus, the new studies herein provide the basis of intervention in the development and progression of tauopathies by using modulators of CRF-R signaling to prevent phosphorylated tau protein accumulation. However, the increase in tau phosphorylation induced by physiological stress (e.g. LPS induce immune challenge) did not appear to be CRFR dependent (FIG. 9A-B). It suggests that CRFR involvement may be limited to emotional stressors.

Previously, there has been a lack of therapies that are effective to reduce initial protein aggregation or prevent further accumulation of aggregated proteins in tauopathies. Therapies that would reduce tau protein accumulation are of great interest since they have the potential to delay the onset of disease and/or slow disease progression. Furthermore, therapies that target tau protein accumulation may be applicable to a wide range of disorder (tauopathies) that involve tau protein accumulation despite having disparate etiologies, symptoms and sites of action. To this end the instant invention provides methods for antagonizing the CRF-R1 signaling pathway and/or agonizing CRF-R2 signaling to reduce stress-induced tau protein phosphorylation. Since chronic stress is demonstrated to result in accumulation of insoluble permanently phosphorylated tau proteins, methods of the invention may be used to prevent the accumulation or tau protein aggregates and/or to slow the growth of such aggregates. Thus, methods provided herein may be employed to delay the progression or onset of tauopathy by decreasing the rate of tau aggregate accumulation.

Previous, in vitro studies regarding the role of CRF-R signaling in AD had suggested that CRF-R1 agonists might be used to protect neuronal cells from toxic effects of protein aggregates. However, these in vitro studies failed to recognize a role of CRF signaling in stress induces tau phosphorylation and ultimately in tau accumulation. Thus, the instant invention also provides an animal model system for screening new molecules that may be used to modulate stress induced tau protein phosphorylation. This new system may be used to determine the effect of candidate molecules on both transient and chronic stress induced tau protein phosphorylation and thus provides a platform to identify molecules can be used to reduce the accumulation of tau protein that may result from long term/chronic stress conditions. Furthermore, methods for determining optimal dosage ranges for candidate molecules are also provided. For example, the techniques may be used to identify a dosage range that partially reduces transient tau protein phosphorylation during stress, while greatly reducing permanent tau phosphorylation or insoluble tau accumulation as a result of chronic stress conditions.

I. Tau Protein and its Signaling Pathway

Tau normally serves to bind and stabilize neuronal microtubules, to facilitate their roles in cellular structure, polarity and transport (Stamer et al., 2002). Recent work suggests that tau plays a beneficial role in supporting normal hippocampal memory-related function (Boekhoorn et al., 2006). Phosphorylation can disrupt these activities and promote cytoskeletal destabilization (Sengupta et al., 1998). Aberrantly phosphorylated forms of tau aggregate into PHFs, and these into insoluble NFTs, a defining feature of AD (Kopke et al., 1993). In this light, the observation that acute stress results in tau-P at AD-relevant sites defines one potential means by which stress exposure may translate into neuropathology. This effect has previously been reported a range of relatively strenuous challenge conditions, including heat shock (Papasozomenos, 1996), starvation (Yanagisawa et al., 1999; Planel et al., 2001, 2004), forced swimming in cold water (Korneyev et al., 1995; Korneyev, 1998; Okawa et al., 2003; Feng et al., 2005; Yoshida et al., 2006), glucoprivation (Planel et al., 2004), ether inhalation (Ikeda et al., 2007), and during hibernation (Arendt et al., 2003; Hartig et al., 2007). It is now common in the field of stress neurobiology to distinguish two broad categories of stress models. These may be termed "physiological" and "emotional", and are distinguished by the nature of the sensory input that registers the challenge, the global pattern of activational responses they induce within the brain, the extent to which they invoke affective responses, and the circuitry that mediates certain adaptive responses to them (Sawchenko et al., 1996; Watts, 1996; Herman and Cullinan, 1997; Dayas et al., 2001). Whereas the stressors shown previously to elicit stress-induced tau-P either are known, or may reasonably be assumed, to fall in the physiological category, the restraint model employed herein is a prototypic emotional stress paradigm. Because established models of anxiety (elevated plus maze exposure), fear (open field exposure, conditioned fear) and social stress (social defeat, isolation), share with restraint such key features as a capacity to activate a stereotyped set of interconnected cell groups in the limbic forebrain (Duncan et al., 1996; Campeau et al., 1997; Martinez et al., 2002), the present findings suggest that the generality of stress-induced tau-P may extend into the realm of life stresses encountered in everyday experience.

Several stresses shown previously to elicit tau-P are associated with marked reductions in body temperature (7-10° C.), which can differentially modulate tau kinase and phosphatase activities, leading to the hypothesis that hypothermia may be a common underlying mechanism (Planel et al., 2001; Planel et al., 2004). Restraint protocols like the one employed in the present study also result in reduced core temperature, though of lesser magnitude (0.5-2° C.; Clement et al., 1989; Turek and Ryabinin, 2005; Meijer et al., 2006). It remains to be determined whether the strong correlation between body temperature and tau-P noted in other paradigms (Planel et al., 2007) extends to restraint and emotional stressors in general.

Tau isoforms are single gene products that differ by the inclusion of inserts in an N-terminal projection domain and tandem repeats within a C-terminal microtubule-binding domain (Goedert et al., 1989). Whereas human tau is normally phosphorylated at 2-3 moles/mole of protein, PHF-tau from AD brain is hyperphosphorylated at a 7-10 molar ratio (Kopke et al., 1993). Murine tau can be phosphorylated and form PHFs, in vitro (Kampers et al., 1999). The inventors find that restraint provokes increased phosphorylation at each of seven epitopes examined, all but one of whose responses is differentially modulated by CRFR status. Coupled with the finding that central CRF administration provokes PHF-1 phosphorylation in a CRFR1-dependent manner, we suggest a mechanism involving mediation by CRFR1, which is normally restrained by CRFR2-based signaling.

Two aspects of our findings warrant further consideration. First, CRFR2-deficient mice displayed exaggerated responses to stress at five of seven phosphorylation sites and in three activated kinases. While supporting an interaction with CRFR1 in regulating tau-P, the extent to which these represent convergent or parallel effects is uncertain. In preliminary studies, we find that mice deficient in both CRFRs fail to manifest acute restraint-induced tau-P, supporting some degree of interdependence (Rissman and Sawchenko, unpublished observations). This interpretation is consistent with evidence that CRF, but not CRFR1 expression or ligand binding, is upregulated in some brain regions of CRFR2-deficient mice, and that CRFR1 antagonists can block aspects of the behavioral phenotype of these mutants (Kishimoto et al., 2000; Bale and Vale, 2003). These results suggest that exaggerated stress-induced tau-P seen in CRFR2 mutants is not likely to result from alterations in CRFR1 expression or distribution. Second, while the consistent lack of stress responsiveness of CRFR1 null mice may suggest a target for intervention in tau pathologies, this is offset by a tendency toward increased basal levels of tau-P (AT8 and PHF-1 sites) and activated kinase (notably JNK) expression in CRFR1 mutants. In addition, the need to supplement CRFR1-deficient mice with corticosterone during the perinatal period may complicate interpretation because it exposes the animals to higher glucocorticoid levels during their stress-hyporesponsive period (Baram et al., 1997) and the switch in the dominant form of tau from the 3-repeat to the 4-repeat isoform that occurs at this time (Kosik et al., 1989). It is noteworthy in both respects that acute pharmacological interference with CRF-R1 blocked restraint-induced increments in tau-P without affecting basal levels, suggesting that the elevated baselines seen in knockouts may be a secondary or indirect consequence of chronic receptor deficiency.

Mice deficient in CRF-R1 exhibit impaired hormonal and behavioral responses to stress, while CRF-R2 knockouts are over-reactive on many of the same measures (Smith et al., 1998; Timpl et al., 1998; Bale et al., 2000; Coste et al., 2000; Kishimoto et al., 2000). Subsequent work indicates that CRF-R interactions are not necessarily starkly differential, but has generally supported convergent influences of the two receptor mechanisms on a range of stress-related endpoints (Bale and Vale, 2004). CRF-R1 mRNA is prominently expressed in the pyramidal layer of Ammon's Horn, and in the hilar region of the dentate gyrus, whereas CRF-R2 transcripts are weakly expressed throughout the principal cell layers of both structures (Van Pett et al., 2000). Unfortunately, the lack of validated antisera has precluded decisive histochemical characterization of receptor protein disposition. With respect to ligands, it is unknown whether extrinsic CRF-containing inputs to hippocampus exist, leaving local interneurons (Chen et al., 2004) and the cerebrospinal fluid (Arborelius et al., 1999) as potential sources for delivery of CRF to hippocampal CRF-Rs. Among the urocortins, only a very sparse urocortin 1-immunoreactive input to hippocampus has been documented, likely originating from the midbrain Edinger-Westphal nucleus (Bittencourt and Sawchenko, 2000). Overall, while local receptor mechanisms are in place, the sources of peptides in a position to interact with them are unclear. The apparent paucity of CRF-R2 ligands in hippocampal afferents suggests that their hypothesized interaction with CRF-R1-dependent mechanisms may occur outside the hippocampus, proper.

Signaling Intermediates

Complementary monitoring of the activation state of tau kinases identified several candidate effectors. GSK-3β has been implicated in catalyzing tau-P at $S_{199}$, $S_{212}$, $T_{231}$, $S_{396}$ and, to a lesser extent, $S_{202/T205}$, and confers PHF-like changes (Liu et al., 2003). Its activity is stimulated or inhibited by phosphorylation at $Y_{216}$ and $S_9$, respectively (Cohen and Frame, 2001). Herein it is shown that stress-induced increments in activated GSK-3β whose time course and genotype dependence paralleled tau-P responses, without significant variation in the inhibitory form (Okawa et al., 2003) or total (unphosphorylated) GSK3. The signaling intermediates that may link CRFR ligand binding to alterations in GSK3 activity remain to be identified. Though commonly associated with a Gs-cAMP-protein kinase A mechanism, other signaling pathways can be activated downstream of CRFRs by different G proteins in a cell type- and ligand-dependent manner (Grammatopoulos and Chrousos, 2002; Arzt and Holsboer, 2006; Hillhouse and Grammatopoulos, 2006). Contributing to the lack of clarity is a lingering uncertainty as to the proximate mechanism of tyrosine phosphorylation of GSK, with some reports identifying this as an autophosphorylation event (Cole et al., 2004), and others implicating distinct tyrosine kinases, including Pyk2 and the src-related kinase, Fyn, in this regard (Lee et al., 1998; Hartigan et al., 2001).

In addition to GSK modulation, similar stress- and genotype-dependent changes were observed in levels of activated JNK, implicated in mediating tau-P at the AT8 and PHF-1 epitopes (Atzori et al., 2001). High basal levels of phospho-JNKs in CRF-R1-deficient mice paralleled, and may explain, elevated AT8 and PHF-1 phosphorylation in this same group. The MAP kinases, ERK1 and 2, which can target all tau sites examined here except T231 (Drewes et al., 1992), were relatively unresponsive. Relative levels of cdk5, considered a major tau kinase active at T231, AT8 and PHF-1 sites (Patrick et al., 1999), were also stable across conditions, but one of its activator proteins, p35, exhibited strong CRFR-dependent stress responsiveness. In line with previous findings (Okawa et al., 2003), we did not detect the truncated p35 product, p25, which is a more potent cdk5 activator (Patrick et al., 1999).

Alterations in the activity of tau phosphatases, notably PP2A, have also been implicated in stress-induced tau-P (Planel et al., 2001, 2004). Here we find increased relative levels of the catalytic subunit of PP2A after repeated stress, a finding that has been associated with diminished enzymatic activity in vivo (Planel et al., 2001) and in vitro (Baharians and Schonthal, 1998), and attributed to a potent autoregulatory mechanism. Our failure to discern an acute stress effect on PP2A-c levels is not necessarily indicative of a lack of phosphatase involvement under these conditions.

Effects of Repeated Stress

Acute stress-induced tau-P has been consistently characterized as a transient and reversible phenomenon. As such, it would seem well positioned to contribute to the rapid dendritic/synaptic remodeling seen in the hippocampus in response to stress (Fuchs et al., 2006), but its relevance to longer-term pathogenesis has remained uncertain (see FIG. 8). The present finding that repeated stress exposure results in sustained elevations in tau-P, a portion of which is sequestered in a detergent-soluble form, supports such a potential, as the bulk of dispersed PHFs from the AD brain reside in this same fraction (Iqbal et al., 1984; Rubenstein et al., 1986).

II. Amyloid Beta Pathology

The presence of amyloid plaques in hippocampus, neocortex, and amygdala is another major pathological hallmark of Alzheimer's disease. The principle component of amyloid plaques is the amyloid beta (Aβ) peptide. Aβ is a peptide comprising 39 to 43 amino acids, processed from the amyloid precursor protein (APP), a transmembrane glycoprotein. APP is expressed ubiquitously and is highly conserved in vertebrates. Aβ peptide is generated by the successive cleavage action of β and γ secretases. The β secretase cleaves at the carboxyl-terminal end of the APP, whereas the γ secretase truncates APP at the amino-terminus. The cleavage processing of the APP can generate a number of isoforms of Aβ, ranging from 39 to 43 amino acid residues in length. The most common isoforms are 40 amino acids form (Aβ40) and 42 amino acids form (Aβ42). The Aβ42 form is the more fibrillogenic and is associated with diseases genesis.

Two lines of evidence relate APP processing to repeated stress paradigms. First, an isoform of Glycogen synthase kinase 3 (GSK-3α) has been found to be required for maximal APP processing and Aβ production (Phiel et al., 2003). Both isoforms of GSK-3 are found to be able to phosphorylate tau. Although GSK-3β is more heavily studied in tau pathology because of its localization as a component of NFTs and its propensity to induce tangle pathology (Rankin et al., 2007), an analysis of kinase modulation indicated that GSK-3α is as potently activated by acute restraint as GSK-3β. In addition, the response of both isoforms shows a similar and differential dependence on CRFR status. Second, a recent report documented that restraint stress, or central CRF administration, can increase interstitial fluid levels of Aβ albeit in APP transgenic mice (Kang et al., 2007).

III. Modulation of CRF-R Signaling

A. Small Molecule Drugs

A wide array of CRF-R1 specific antagonist have been developed and are implicated for the treatment of a number of disorders such as mood disorders (affective disorders) and irritable bowel syndrome (see for example, Tache et al., 2004). Preferably, a small molecule CRF-R1 antagonist or CRF-R2 agonist of the invention is water soluble and may be administered orally. Even more preferably, a small molecule for use in the invention is able to traverse the BBB.

A number of small molecule selective CRF-R1 antagonist are also known in the art. For example, MTIP, 3-(4-Chloro-2-Morpholin-4-yl-Thiazol-5-yl)-8-(1-Ethylpropyl)-2,6-Di-methyl-Imidazo[1,2b]Pyridazine is a CRF-R1 selective antagonist with no detectable activity on CRF-R2 that has been implicated for the treatment of alcoholism. Advantageously, MTIP also has favorable solubility and has the ability to cross the BBB (Gerhlert et al., 2007). Compounds like DMP696 ([4-(1,3-dimethoxyprop-2-ylamine)-2,7-dimethyl-8-(2,4-di chlorophenyl)-pyrazolo[1,5-a]-1,3,5-triazine]), DMP904 ([4-(3-pentylamino)-2,7-dimethyl-8-(2-methyl-4-methoxyphenyl)-pyrazolo[1,5-a]-pyrimidine]) and derivatives are known to have >1,000 for selectivity for CRF-R1 relative to CRF-R2 (Li et al., 2005). Another group of CRF-R1 antagonists includes but is not limited to CP-154, 526 and its methyl analog antalarmin (Keller et al., 2002).

Still other CRF-R1 antagonists contemplated for use herein are imidazolyl derivatives such as those described in U.S. Pat. No. 7,125,990. For example, an orally active CRF-R1 selective antagonist R121919 (NBI 30775) has been developed to treat sleep disorders and depression (Chen & Grigoriadis, 2005; Heinrichs et al., 2002). Still further CRF-R1 antagonists contemplated for use herein include but are not limited to R-278995, DMP-696, NBI 27914, NBI-35965, R121920, CRA1000, CRA1001, SSR125543A, DMP 695, DMP 904 and SN003 (McCarthy et al., 1999; Heinrichs et al., 2002; Million et al., 2003; Gilligan et al., 2000; Zorrilla et al., 2003; Holmes et al., 2003).

B. Peptide and Polypeptide Agonist and Antagonists

As discussed above, in some respects CRF-R agonists or antagonist comprise CRF family members or derivatives thereof. For instance, a modified CRF family member may bind to CRF-R1, however not activate or minimally activate CRF-R1 signaling. In still further cases, a modified CRF peptide or polypeptide may bind to and agonize CRF-R2. As described supra, in preferred aspects a CRF-R agonist or antagonist for use according to the invention will be selective for CRF-R1 or CRF-R2 and have little or no activity relative to the other receptor.

A variety of CRF family members are known that can be modified in order to act as antagonists or antagonist. These molecules can be derived from the CRF family member of variety of organisms such as mice, rats, humans and frogs. Some non limiting examples of CRF family members include human and mouse Ucn 3 (SEQ ID NO:1 and SEQ ID NO:2) and human and mouse Ucn 2 (SEQ ID NO:3 and SEQ ID NO:4). For example, the skilled artisan will recognize that in some instances a human or murine Ucn 2 or Ucn 3 may be used as a CRF-R2 agonist according to the invention. Furthermore, modifications of CRF family members may comprise amino acid deletions, amino acid insertions, amino acid substitutions and/or chemical changes, such as the insertion of lactam bridges, acetylation of amino acid side chains or addition of PEG to the polypeptide. In general, modification are made to accomplish one or more of the following; to alter CRF-R activation by the molecule, to enhance the molecules ability to block CRF-R agonism or antagonism, to enhance CRF-R binding or selectivity of the molecule, to modify the pharmacokinetics of the molecule. Thus, it will be understood that while any CRF family member can be modified in order to generate a CRF-R agonist or antagonist, CRF family members with high affinity for CRF-R2 are preferred as CRF-R2 agonists.

It is also contemplated that in certain embodiments modified CRF family member will preferentially agonize specific CRF-R2 protein isoforms. For example, the affinity of modified CRF family members for the alpha, beta and/or gamma protein isoforms for CRF-R2 can be assessed and CRF-R2 agonists that are specific for one or more of the isoforms can be selected. This may be of particular advantage since it is known that the expression of the various CRF-R2 isoforms is variable through-out the body and thus by targeting specific CRF-R2 isoforms organs or tissues expressing that isoform (e.g., the CNS) may be more specifically targeted. Again, this kind of specific CRF-R2 isoform targeting can both increase the efficacy and decrease potential side effects of CRF-R2 agonists.

In additional aspects of the invention CRF polypeptides may be further modified by amino substitutions (e.g., to enhance selectivity for CRF-R1 or CRF-R2) for example by substituting an amino acid at one or more positions with an amino acid having a similar hydrophilicity. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in CRF-R antagonist or agonist and will likely only have minor effects on their activity and ability to bind CRF-R. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the polypeptide CRF-R antagonist or agonist described herein may be modified by the substitution of an amino acid, for different, but homologous amino acid with a similar hydrophilicity value. Amino acids with hydrophilicities within +/−1.0, or +/−0.5 points are considered homologous.

It will also be understood that certain amino acids have specific properties, and thus any amino acid substitution will abolish said property. For example cysteine residues have the unique ability to form disulfide bonds, that can be crucial for protein structure and activity. Thus, a substitution of cysteine residue for any other amino acid may be expected, by one of skill in the art, to alter the activity of a protein. Additionally, certain CRF-R agonists and antagonists are may also comprise a lactam bridge that structurally constrain the polypeptide. Such lactam bridges can be formed between Glu and Lys residues in a protein, and thus in certain cases amino acids may be substituted for a Glu or a Lys in order to facilitated the insertion of a lactam bridge. Such lactam bridges have been shown to be very effective in the generation of CRF-R2 binding peptides as described in Rivier et al., 2002. Therefore in certain embodiments specific amino acids may be substituted for unlike amino acids in order to facilitate the insertion of an amino acid with a desired chemical or structural property, such as a lactam bridge.

In certain embodiments of the current invention CRF-R agonists or antagonists comprise antibodies that bind to CRF-R2 or CRF-R1. CRF-R antibodies may comprise polyclonal and/or monoclonal antibodies or fragments thereof. Methods for generating antibodies are well know to those in the art. In general antibodies are raised against an antigen that comprises at least a portion of a CRF-R amino acid sequence. Thus it will be understood that antibodies can be raised against the complete CRF-R amino acid sequence or portions thereof and that the amino acid sequence from any of the CRFR2 protein isoforms (alpha, beta and/or gamma) may be used as the immunogenic antigen. Furthermore, CRF-R derived amino acid sequence may be further coupled to additional amino acid sequences to increase its antigenicity.

In certain cases, CRF-R2 antibodies may bind preferentially to certain CRF-R2 protein isoforms (e.g. CRF-R2 alpha). In some preferred cases CRF-R2 antibodies can be made that bind to only one of the CRF-R2 protein isoform. Such antibodies may have the advantage of being able to target specific tissue and/or organs and therefore providing highly specific kinds of CRF-R2 agonists.

Not all antibodies that bind to CRF-R will act as agonists or antagonists thus in many cases the ability of an antibody to block CRF-R1 agonism or mediate CRF-R2 agonism (e.g., an anti-idiotypic antibody) can be tested. Any of a variety of screening assays well known in the art may be used to test CRF-R agonist or antagonist activity of antibodies (e.g., see the binding assays described by Rivier et al. 2002). Some specific methods for testing the efficacy of antibody agonists/antagonists in vivo are described in examples provided here.

In certain further aspects of the invention CRF-R antibodies may be modified to enhance their efficacy as CRF-R agonists/antagonists. For example, it is preferred that polypeptide therapeutics do not elicit an immune response. Thus, in the case where the subject for treatment is a human, antibodies may be human antibodies or humanized antibodies, so as to reduce the possibility of immune response. In yet further embodiments, it may be preferred that antibodies be single chain antibodies since the manufacture of single chain antibodies can be substantially streamlined by production in insect or bacterial expression systems. Thus, in certain cases, CRF-R antibodies that act as agonists or antagonists may be sequenced and the sequence used to generate single chain antibodies.

It is additionally contemplated that nucleic acid aptamers that bind to CRF-R may be used to agonize or antagonize CRF-R activity. Methods for selecting aptamers by using recombinant CRF-R or fragments thereof to purify nucleic acid aptamers from a library, are well known in the art. The technique known as SELEX and can also be automated to enhance the speed and efficacy of selection, for example see U.S. Pat. Nos. 6,569,620 and 6,716,580. Aptamers identified to bind to CRF-R can then be screened for the ability to agonize or antagonize CRF-R1 or CRF-R2. In some specific cases, aptamers may be negatively selected using one CRF-R protein (or protein isoform) and then positively selected using a different CRFR2 protein (or protein isoform) in order to identify aptamers that specifically bind to particular CRF-R protein or isoforms. As used throughout the specification, "positive selection" means collecting molecules that bind to particular target, while "negative selection" means collecting molecules that do not bind to a particular target. Aptamers according to this aspect of the invention may be DNA or RNA, and preferable comprise modified nucleotides that inhibit degradation thereby enhancing activity.

Methods for synthesizing and purifying nucleic acids, such as CRF-R binding aptamers are well known to those in the art. For example DNA aptamers may be synthesized by PCR, while RNA aptamers can be generated by in vitro transcription. In preferred embodiments, large scale preparation of aptamers may be accomplished by chemical synthesis, this method allows for DNA, RNA and chemically modified oligonucleotides to be incorporated into to the specific aptamer sequence.

IV. Therapeutic Compositions and Methods

Pharmaceutical compositions of the present invention comprise, in some instances, an effective amount of a CRF-R1 antagonist and/or a CRF-R2 agonist in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains CRF-R agonists/antagonists or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, targeting agents (e.g., CNS targeting agents), lubricants, sweetening agents, flavoring agents, gels (e.g., gelatin), dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

A therapeutic composition of the invention may comprise different types of carriers depending on whether it is to be administered in solid, liquid or aerosol form, and whether it need to be sterile. The present invention can be administered intravenously, intradermally, intraarterially, intraperitoneally, intracranially, mucosally, intraocularally, subcutaneously, or intranasally, intravitreally, intravaginally, intrarectally, topically, intrathecally, intracerebroventricularly, orally, locally (e.g., into the CNS), via inhalation (e.g., aerosol inhalation), via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a subject can be determined by physical and physiological factors such as body weight, severity of condition, the type of disease being treated (i.e., type of tauoopathy), previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In the case, of proteinacious compositions of the invention is may also be preferable that the action of proteases be inhibited during storage of compositions. This can be accomplished by the additional of protease inhibitors and/or the storage of the compositions at low temperature prior to administration.

In embodiments where compositions according to the invention are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

A. Dosages

CRF-R agonists/antagonists of the invention will generally be used in an amount effective to achieve the intended purpose. For use to treat or delay the onset or progression of a tauopathy, the molecules of the invention, or pharmaceutical compositions thereof, are administered in a therapeutically effective amount. A therapeutically effective amount is an amount effective to ameliorate or prevent the symptoms, or onset or progression of clinical disease of, the subject being treated. Determination of a therapeutically effective amount is well within the capabilities of those skilled in the art, especially in light of the detailed disclosure provided herein. For example, as described supra, in certain instances an effective amount of a compound of the invention may be defined by the ability of the compound to prevent a given amount of stress-induced tau phosphorylation.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art and the specific techniques described herein. One having ordinary skill in the art could readily optimize administration to humans based on animal data.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable (e.g., to prevent to onset of symptoms). The therapy may be provided alone or in combination with other drugs. In the case of AD, the drugs that may be used in combination with Aβ vaccines (e.g., see U.S. Pat. No. 6,787,140 and PCT publication, WO 2005/014041) an acetylcholinesterase inhibitor such as Donepezil, Rivastigmine or Galantamine, Vitamin E, or an anti-inflammatory drug such as a nonsteroidal anti-inflammatory drug (NSAID) (De La Garza, 2003). Non-limiting examples NSAIDs include, ibuprofen, ketoprofen, piroxicam, naproxen, naproxen sodium, sulindac, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, and magnesium salicylate.

Methods for estimating dose conversions between animal models and humans have previously been developed. In general these algorithms have been used to extrapolate an animal dose to a dose that would be tolerated by a human. For example, methods for dose conversion have previously been disclosed by Freireich et al. (1966). The conversion methods taught by Freireich calculate equivalent doses between species using surface area ($m^2$) rather than mass (kg), a method that correlates much more closely to actual data than body mass conversions. Specifically, Freireich teaches how to use an animal 10% lethal dosage ($LD_{10}$) value to estimate the maximum tolerated doses in a human. Freireich also discussed method for converting a dose in mg/kg to a dose in mg/$m^2$ by using the "km" conversion factor for the given animal. For example, in the case of a laboratory mouse the km is approximately 3.0. Thus, in mice mg/$m^2$=km (3.0 for mice)×dose in mg/kg.

More recent studies regarding species dose scaling have further elaborated upon the methods of Freireich. These newer studies have reduced error associated with conversion between species to determine human tolerable doses. For example, Watanabe et al. (1992) describes that a conversion of doses between species using body surface area may not be the most accurate method per se for predicting a human equivalent dosage. Nonetheless, the scaling factors set forth by Watanabe yield results that are with-in the margin of error of the older Freireich conversions. Currently accepted methods for determining a proper starting dose in humans expand upon the methods set forth by Freireich. For example, Mahmood et al. (2003) provides a discussion regarding the choice of a proper starting dose in humans given dose studies in animals.

B. Toxicity

Preferably, a therapeutically effective dose of CRF-R agonist or antagonists described herein will provide therapeutic benefit without causing substantial toxicity.

Toxicity of the molecules described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975).

C. CNS Targeted Therapy

In certain aspects of invention concerns compositions such as CRF-R1 antagonists and/or CRF-R2 agonists that are CNS targeted. A variety of molecules are known to confer CNS targeting. For instance, certain antibodies are know to cross the BBB, thus such antibodies may be used to transport a payload, such as a CRF-R agonist/antagonist to the CNS. Some specific antibodies that may be used include but are not limited to antibodies to transferrin receptors (e.g., OX26) or antibodies to the insulin receptor (Schnyder & Huwyler, 2005). Other polypeptides may also be used to target the CNS such as cationized albumin. Thus, polypeptide CNS targeting agents may in some aspects, be bound to a CRF-R agonist or antagonist for use according to the invention. In some very specific cases, a peptide (or polypeptide) CRF-R agonist or antagonist may be provided as a fusion protein with a CNS targeting polypeptide. In still other cases nanoparticles such as Polysorbate 80-coated polybutylcyanoacrylate nanoparticles may be used to deliver compositions to the CNS (Olivier, 2005). In still further aspects, CNS targeting polypeptides may be conjugated to liposomes to form CNS targeting complexes (Schnyder & Huwyler, 2005). Furthermore, peptide and polypeptide CRF-R1 antagonists and/or CRF-R2 agonists may be targeted to the CNS by glycosylation, for example as described in Egleton & Davis (2005). In yet further aspects, viral vectors may be used to targeted delivery of peptides or polypeptides to the CNS. For example, lentiviral vector systems for polypeptide delivery are known in the art, see for example Spencer & Verma (2007).

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Experimental Methods

CRF-R Knockout Mice

Mutant mice and littermate wild type (wt) controls were bred from heterozygote breeder pairs of established lines derived from backcrosses of founder mice to achieve a pure C57BL/6 background (Smith et al., 1998; Bale et al., 2000). Genotyping was performed by PCR analysis of tail DNA, and appropriate males were used for experimentation at 15-22 weeks of age. Pregnant females bearing fetuses carrying a mutant CRF-R1 allele received drinking water with 10 µg/ml corticosterone from days E12-P14 to prevent early mortality due to pulmonary dysplasia (Smith et al., 1998). Because CRF-R1−/− mice exhibit adrenal cortical agenesis, experimental animals were reinstated on corticosterone supplementation for 21 days prior to testing to allow the normal nocturnal bias in appetitive behavior to approximate the circadian fluctuation in circulating hormone levels. Blood samples were collected at the time of sacrifice and plasma corticosterone levels determined by RIA to assess the effectiveness of the replacement regimen. The Institutional Animal Care and Use Committee of the Salk Institute approved all experimental protocols.

Adrenalectomy (ADX) and Corticosterone Replacement 8-12 week old male wt C57BL/6 mice (Jackson Labs, Bar Harbor, Me.) underwent ADX via bilateral incisions on the dorsolateral flanks under isoflurane anesthesia (to effect; 3-5% vapor/total vol of $O_2$). ADX mice received replacement corticosterone (10 µg/ml; Sigma, St. Louis, Mo.) in drinking water immediately after surgery. Animals were utilized in stress experiments 21d after surgery.

Restraint Stress

Acute restraint stress involved placing mice in ventilated 50 ml conical tubes for 30 min; repeated stress involved 14 consecutive daily exposures. Animals were killed at various intervals ranging from 20 min to 24 hr after stress. Control mice were handled comparably, but were not otherwise manipulated.

Intracereboventricular Injections

CRF-R1−/− (U.S. Pat. No. 6,147,275) and CRF-R2−/− (U.S. Pat. No. 6,353,152) mice, along with age-matched wt controls (n=3/group), were anesthetized with isoflurane, and implanted stereotaxically with 26-ga guide cannulae (Plastics One, Wallingford, Conn.) aimed to terminate above the lateral ventricle. Cannulae were affixed to the skull with dental acrylic adhering to jeweler's screws partially driven into the skull, and sealed externally with stylets. After 7 d recovery, stylets were replaced with 33-ga injection cannulae, and 2 hr later the animals were remotely injected with 0.5 µg synthetic mouse/human CRF in 2 µl saline, or vehicle alone, over ~1 min. To approximate the time frame used in acute stress experiments, animals were killed 40 min after icy injection and perfused for immunohistochemistry, as above. CRF was generously provided by Dr. J. Rivier (Salk Institute).

In Vivo Pharmacology

The small molecule, CRF-R1-selective antagonist, antalarmin (Webster et al., 1996), was administered at 20 mg/kg by intraperitoneal (ip) injection 20 min before stress exposure. All animals were handled twice daily for 28 d prior to experimentation, and received daily mock ip injections to minimize stress of injection at testing. Antalarmin was solubilized in equal volumes of absolute ethanol and Cremaphor EL (Sigma-Aldrich, St. Louis, Mo.), using previously described protocols (Webster et al., 1996; Pernar et al., 2004). This stock solution was diluted in prewarmed (50° C.) distilled water and adjusted to a final concentration of 4 mg/ml immediately prior to injection.

Western Blot Analysis

Mice were deeply anesthetized with sodium pentobarbital (40 mg/kg), which has been demonstrated to not influence the phosphorylation state of tau over the time frame employed here (Papasozomenos, 1996). After sedation, the animals were decapitated and the hippocampus was rapidly dissected and frozen on dry ice. Hippocampal tissues were homogenized in RIPA buffer (50 Mm Tris-HCl pH 7.4, 0.1% SDS, 1% NP40, 0.25% sodium deoxycholate, 150 nM NaCl, 1 mM EDTA, 1 mM EGTA, 1 mM $Na_3VO_4$, and 1 µM okadaic acid). Immediately before homogenization, protease inhibitors PMSF, NaF (1 mM), aprotinin, leupeptin, pepstatin (1 µg/ml each) were added. RIPA fractions were obtained by centrifuging twice at 40,000 g for 20 min, and the supernatant was collected. For analysis of tau solubility (repeated stress), sequential fractionation of RAB and RIPA extracts were performed as described (Higuchi et al., 2002; Kraemer et al., 2003). In this case, tissues were first homogenized in high-salt RAB (0.1 M MES, 0.75 NaCl, 1 mM EGTA, and 0.5 mM $MgSO_4$) and then centrifuged at 40,000 g for 40 min. The resultant supernatant was collected (soluble RAB fraction). Resultant pellets were resuspended in RIPA buffer as described above to obtain detergent-soluble fractions. Protein concentrations were determined using a BCA Protein Assay Kit (Pierce Biotechnology, Rockford, Ill.). Proteins were then boiled in sample buffer containing SDS, 2-mercaptoethanol, and glycerol at 95° C. for 5 min. 6 µg of protein was then loaded and electrophoretically separated on a 12% SDS-polyacrylamide gel. Proteins were transferred to nitrocellulose membrane (0.2 µm, BioRad, Hercules, Calif.) and incubated in primary antibodies diluted in 5% milk-PBS-T overnight at 4° C. Primary antibodies were detected with either anti-mouse or rabbit horseradish peroxidase-linked secondary antibodies (1:1000

Calbiochem, San Diego, Calif.) and developed with an enhanced chemiluminescence Western blot detection kit (Supersignal West Pico, Pierce Biotechnology). Background subtraction was performed and quantitative band intensity readings were obtained using NIH Image software.

Antibodies

Well-characterized phospho-specific antibodies were used for detection of several phosphorylated residues on mouse tau. For Western blots, $T^{181}$, $S^{199}$, $S^{212}$, $T^{231}$, $S^{422}$ (1:1000, Biosource), $S^{202}/T^{205}$ (1:500, AT8, Pierce Biotechnology), $S^{396/404}$ (1:1000, PHF-1, gift from Dr. P. Davies). These antibodies were chosen based on their ability to resolve target bands at the appropriate molecular weight for phosphorylated tau (i.e., ~50-75 kDa). Phospho-specific antibodies against $S^{217}$, $S^{262}$, $S^{356}$ and $S^{409}$ phosphorylated tau (Biosource) were also tested. Immunohistochemical analyses used PHF-1 for detection of phosphorylated tau. Specificity of PHF-1 for phosphorylated tau in mouse tissue was confirmed by pretreating sections from stressed mice with alkaline phosphatase (40 mg/ml, Sigma-Aldrich). This treatment eliminated detectable PHF-1 labeling in all experimental groups. For assessment of tau kinases, specific antibodies either to phosphorylation sites or activator proteins were used. For glycogen synthase kinase (GSK-3), total GSK-3β (1:2500, BD Transduction Labs, San Diego, Calif.), activated GSK-3β (pY216, 1:1000, BD Transduction Labs), inactive GSK-3β (pS9, 1:1000, Cell Signaling), cyclin-dependent kinase 5 (cdk-5; 1:1000; Calbiochem, San Diego, Calif.), cdk5 activator proteins, p25 and p35 (1:1000, Santa Cruz Biotechnology, Santa Cruz, Calif.), phosphorylated c-Jun-N-terminal kinase (JNK, 1:1000; Cell Signaling, Danvers, Mass.), mitogen activated protein kinases (ERK 1/2, 1:500, Cell Signaling), the catalytic subunit of protein phosphatase 2A (PP2A-c, 1:5000, BD Transduction Labs). β-actin (1:2000, Sigma-Aldrich) was used as a control for protein loading.

Immunohistochemistry

Mice were perfused with 4% paraformaldehyde, as previously described (Bittencourt and Sawchenko, 2000). 30 μm-thick frozen sections were cut on a sliding microtome and stored at −20° C. in cryoprotectant solution (20% glycerol and 30% ethylene glycol in 0.1 M phosphate buffer) until use. Free-floating sections containing the hippocampus were used to detect tau-P with PHF-1 (1:500) in mouse tissues using Mouse-on-Mouse Immunodetection Kit reagents (Vector, Burlingame, Calif.) to avoid detection of endogenous mouse immunoglobulin. Endogenous peroxidase was quenched with 0.3% hydrogen peroxide, followed by 1% sodium borohydride to reduce free aldehydes. Reaction product was developed using a nickel-enhanced glucose oxidase method (Shu et al., 1988).

Statistical Analyses

Integrated intensity readings from Western blots were analyzed using either a one- or two-way ANOVA using Prism4 Software (GraphPad, San Diego, Calif.). Resultant data were plotted on bar graphs, with data expressed as mean±SEM percentage of control values.

AD Transgenic Mice

The PS/APP mouse line was originally purchased from another research laboratory. These mice express the Swedish familial AD mutation of human amyloid precursor protein (APP) (APPK670N,M671L; line Tg2576) and the familial AD mutation of presenilin-1 (PSEN1-dE9) (Jankowsky et al., 2001). Hemizygous double mutant PS/APP offspring and non-transgenic mice were used in experimentation, as it has been reported that homozygote lines of Tg2576 cannot be generated (McGowan et al., 1999). Genotypes were determined by PCR analysis of ear or tail DNA.

Lipopolysaccharide (LPS) Injection Induced Physiological Stress

Animals adapted to handling and intraperitoneal (ip) injection were administered LPS from *Salmonella typhimurium* (Sigma-Aldrich, St. Louis, Mo.) at 10 μg/kg, ip in 100 μl sterile saline. Control animals were pretreated similarly and received injections of vehicle.

Systemic Antagonist Administration

For acute stress experiments, CRFR1-selective small molecule antagonist, antalarmin (Webster et al., 1996), was administered at 20 mg/kg by intraperitoneal (ip) injection 20 min before stress exposure. All animals were handled twice daily for at least 14d prior to experimentation, and receive daily mock ip injections to minimize stress of injection at testing. Antalarmin was solubilized in equal volumes of absolute ethanol and Cremaphor EL (Sigma-Aldrich, St. Louis, Mo.), as described (Webster et al., 1996; Pernar et al., 2004). This stock solution was diluted in prewarmed (50° C.) distilled water and adjusted to a final concentration of 4 mg/ml immediately prior to injection. For chronic administration, antalarmin was administered twice daily via ip injection (Wong et al., 1999).

Chronic Variable Stress (CVS)

CVS involved daily exposure to either two brief or one sustained stressor over 15d. Brief stressors included elevated plus maze exposure (30 min), shaker stress (30 min on an orbital shaker at 100 rpm), ip hypertonic saline injection (0.4 ml of 1.5M saline), restraint (30 min), tail suspension (10 min) and forced swimming (10 min in RT water). Sustained stressors included social isolation (single housing for 1d), wet bedding (1d), and cold exposure (8 hr at 5-7° C.). Stressors were presented at unpredictable times of day and in random sequence.

Electron Microscopy

Negative staining and immunogold labeling was carried out in extracts deposited on carbon-coated grids (400m, Pelco, Clovis, Calif.), which has been exposed to glow discharge for 5 min. At each step, excess liquid was removed by wicking with bibulous filter paper. Grids were placed sequentially on drops of reagents spotted on parafilm. Except for the samples, all reagents were 0.2 μm filtered. The grids were placed on 10 μl of a sample for 90 seconds. The grids were then blocked with 2% BSA, 0.1% fish gelatin in KPBS for 10 minutes, which was followed by a treatment with 20 μl primary antibody (e.g., anti-PHF-1 at 1:100) in blocking buffer for overnight at 4° C., in a sealed, humidified chamber. The next day, the grids were washed 3 time for 5 minutes each in blocking buffer, and placed on 20 μl secondary antibody at 1:50 (goat anti-mouse IgG coupled to 10 nm gold particles, BioCell, Rancho Dominguez, Calif.) for 2 hr at room temperature. The grids were then washed 3 times for 5 minutes each in blocking buffer, and washed 3 times for 5 minutes in water. Following the wash, the grids were stained for 60 seconds with 2% phosphotungstic acid pH 7.0 or 4% uranyl acetate, and dried with filter paper, followed by an air dry treatment. After the preparation, the samples were examined in a JEOL 100 CX II transmission electron microscope (JEOL USA, Inc., Peabody, Mass.).

ELISA

Soluble, detergent-soluble, and formic acid soluble fractions were extracted from stressed mice for ELISA assay for Aβ using reagents available in kit form (Biosource mouse β-amyloid colometric immunoassay kit, Invitrogen, Carlsbad, Calif.). Extract preparation is detailed above. Formic acid extraction involved solubilization of detergent-insoluble pellets with 70% formic acid and subsequent centrifugation at 40,000 g for 20 min. Data were read at 450 nm using a BioRad Lumimark Plus Microplate reader (BioRad, Hercules, Calif.) attached to a PC computer with Microwin software (MicroWin AG, Wallisellen, Switzerland).

Example 2

Tau Protein Phosphorylation after Acute Restraint Stress

Figure 1:
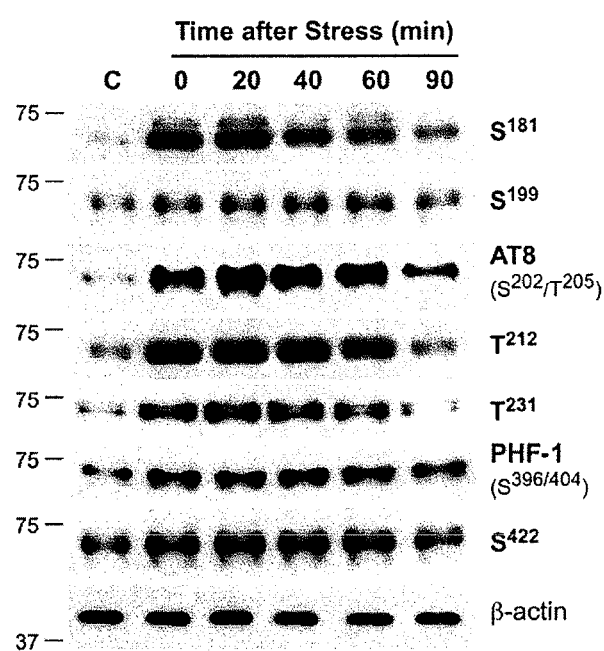
FIG. 1: Time course of stress-induced tau phosphorylation. Western blots of hippocampal extracts probed for tau-P at select AD-relevant sites in unstressed controls (C) and mice sacrificed 0, 20, 40, 60 or 90 min after a single 30 min exposure to restraint stress. For all epitopes examined, signal under basal conditions was low, but rose immediately after stress to levels that were markedly increased (2-10 fold) over control levels through 60 min, and diminished thereafter. The 20 min post-stress time point was adopted for use in subsequent experiments. β-actin was used as a loading control.

To determine whether increased tau phosphorylation (tau-P) was observable in response to acute restraint, an acknowledged "emotional" stressor (Sawchenko et al., 2000). Western blot analysis was used to examine tau phosphorylation at several AD-relevant N- and C-terminal sites ($S^{181}$, $S^{199}$, $S^{202}/T^{205}$ (AT8), $T^{212}$, $T^{231}$, $S^{396/404}$ (PHF-1), and $S^{422}$) in hippocampal extracts from C57BL/6 mice sacrificed at various intervals after a single 30-min episode of restraint stress. Relative to basal (non-stressed) values, all sites exhibited significant increases in phosphorylation that were apparent at the termination of stress (0 min), with peak elevations (2-10 fold) achieved 20-40 min later and sustained through 60 min (FIG. 1). By 90 min, levels were reduced to or near those of unstressed controls. These results demonstrate that a representative emotional stressor induces rapid and reversible increases in tau-P at multiple AD-relevant sites. Increments in tau-P were quite stable over 20-60 min post-stress, and the 20 min time point was selected for use in subsequent analyses.

Example 3

Glucocorticoid Involvement in Stress-Induced Tau Phosphorylation

Because of the dominant role of glucocorticoids in mediating stress effects on the CNS and their implication in AD neuronal damage (Sapolsky et al., 1985, 1986) and in mouse models of AD (Green et al., 2006), studies were undertaken to determine whether stress-induced tau-P was dependent on stress-induced glucocorticoid secretion. Although a prior study employed immunoassay and found no effect of adrenalectomy (ADX) on PHF-1 reactivity after acute cold water stress (Korneyev et al., 1995), phosphatase inhibitors were not utilized and only soluble fractions of tau proteins were examined. Studies described here examined stress-induced tau-P responses at the AT8 and PHF-1 sites in extracts of hippocampus from ADX and control mice exposed to acute restraint stress (FIG. 2A-B). ADX animals received replacement corticosterone in drinking water (10 µg/ml) to approximate basal hormone titers and their diurnal variation. Robust stress-induced tau-P responses were observed in ADX mice that did not significantly differ from those of intact controls at either the AT8 and PHF-1 phosphorylation sites (each $P>0.10$). These results confirm that acute stress-induced tau-P is not dependent upon glucocorticoid secretion.

Example 4

CRF-Rs Differentially Regulate Stress-Induced Tau Phosphorylation

The CRF family of signaling molecules is broadly involved in physiological and behavioral responses to stress (Chadwick et al., 1993), and is altered early in AD progression (Davis et al., 1999). However, the nature of its involvement in AD neuropathology is unclear. In view of this deficiency, the role of CRF-Rs in acute stress-induced tau phosphorylation was investigated using mice deficient in CRF-R1 (Smith et al., 1998; U.S. Pat. No. 6,147,275) or CRF-R2 (Bale et al., 2000; U.S. Pat. No. 6,353,152). Western analyses (FIG. 3A-B) indicated a tendency for CRF-R1−/− mice to exhibit higher basal levels of tau-P than unstressed wild type (wt) animals at several sites, although this difference was statistically reliable only at the AT8 epitope ($P<0.01$). More importantly, CRF-R1-deficient mice failed to exhibit significant increases in tau-P at any site at 20 min after stress, compared to age-matched wt controls. By contrast, CRF-R2 knockouts displayed normal basal levels of tau-P ($P>0.05$ vs wt), but showed robust responses to acute stress that commonly exceeded those seen in wt animals. Specifically, phosphorylation responses of CRF-R2−/− mice were significantly greater that those of wt animals at the $S^{181}$ ($P<0.01$), $S^{199}$ ($P<0.001$), $T^{212}$ ($P<0.05$), $T^{231}$ ($P<0.05$), and PHF-1 ($P<0.01$) sites. Phosphorylation responses of CRF-R2 null mice at the AT8 and S422 sites did not differ significantly from those of wt stressed animals ($P>0.05$).

To probe the localization of tau-P responses, immunohistochemical methods were used to examine the distribution of PHF-1 phosphorylation, and its stress and CRF-R-dependence. Immunolabeling results were highly compatible with biochemical data in showing prominent upregulation of PHF-1 staining in wt mice in response to stress, which was attenuated and exaggerated in CRF-R1- and CRF-R2-deleted animals, respectively (FIG. 4A). In the dentate gyms of stressed wt animals, PHF-1 positive cell bodies were seen primarily in the hilus (polymorph and subgranular regions), but also in deep aspects of the granule cell layer. PHF-1 positive mossy fibers and a band of punctate (presumably axonal) elements in the inner third of the molecular layer was also observed. In Ammon's Horn, dominant features included labeled perikarya scattered mainly throughout the pyramidal layer and proximal dendritic zones, and bands of axon terminal-like puncta engulfing the pyramidal cell layer and in stratum lacunosum-moleculare. Radially oriented processes, some traceable to labeled cell bodies and presumably representing dendritic labeling, were seen in stressed wt and CRF-R2-deficient animals. Alterations in immunostaining as a function of stress and genotype were manifest as differences in the number and/or intensity of labeled elements, with no discernible differences in distribution.

To determine whether CRF is capable of independently eliciting hippocampal tau-P, wt and CRF-R-deficient mice were implanted with lateral ventricular cannulae for icy injection. Resultant PHF-1 immunoreactivity was examined 40 min after administration of CRF (0.5 µg in 5 µl) or vehicle (FIG. 4B). The general pattern of results was similar to that observed in response to stress, in that wt and CRF-R2−/− mice treated with peptide displayed robust increases in hippocampal tau-P, while labeling in CRF-R1−/− mice was comparable to the low level seen in saline-injected controls. In the dentate gyms, PHF-1 positive cell bodies were seen in the hilus and deep aspects of the granule cell layer (FIG. 4B). In Ammon's Horn, PHF-1 labeling was observed in mossy fibers and in the form of punctate pericellular labeling throughout the pyramidal cell layer and, more sporadically, in the dendritic zone, with particular concentration at the septal pole of the hippocampus. In contrast to stress effects, however, no labeling of pyramidal neurons or their processes was observed after icy CRF injections. These findings indicate that central CRF administration at least partially recapitulates the effects of stress, and demonstrates a similar dependence on CRF-R integrity.

Example 5

Effects of Pharmacologic Blockade of CRF-R1

Interpretation of data derived from conventional knockout animals may be complicated by developmental or indirect effects of lifelong lack of expression of the targeted gene. This is particularly true of CRF-R1-deficient mice, which exhibit chronically impaired pituitary-adrenal function (Smith et al., 1998). Despite efforts to mitigate such effects by steroid replacement perinatally and immediately prior to experimentation (see Example 1), confidence in the assertion of a regulatory role for CRF-R1 in this context would be bolstered if the effects were maintained in the face of acute disruption of receptor function. Therefore, the effect of antalarmin, a small molecule, selective CRF-R1 antagonist (Webster et al., 1996), on basal and stress-induced tau-P was studied. Neither antalarmin nor the vehicle used for its administration significantly altered basal levels of tau-P at the AT8 or PHF-1 sites, relative to untreated controls (FIG. 5). However, antalarmin treatment prevented stress-induced increments in phosphorylation at both sites (lanes 5-6; each $P>0.10$ vs. untreated controls). Phosphorylation responses in stressed, vehicle-treated animals were comparable to those of stressed, untreated controls, and significantly elevated over vehicle control levels ($P<0.01$). These findings support a specific involvement of CRF-R1 signaling in stress-induced tau-P.

Example 6

Modulation of Tau Kinase Activity by Stress and CRF-Rs

To identify potential mediators of acute stress-induced tau-P, antibodies specific to active and inactive states of kinases implicated in tau-P in same tissue extracts were employed to interrogate changes in stress-induced kinase activation, and their CRF-R dependence (FIG. 6). Several kinases examined, including the active (phosphorylated at $Y^{216}$, or $pY^{216}$),) but not the inactive ($pS^9$), or total (unphosphorylated) form of glycogen synthase kinase-3β (GSK-3β), the $pT^{183}/Y^{185}$ form of the 46 and 54 kDa c-Jun N-terminal protein kinases (JNK46/54), and the $pT^{202}Y^{204}$ form of the mitogen-activated protein kinases, ERK2, but not ERK1, displayed upregulation in response to acute restraint. The time courses of stress effects seen on these kinases were similar to those shown in FIG. 1 for stress-induced tau-P. Relative levels of cyclin-dependent kinase 5 (cdk5) were unchanged from steady state over the post-stress intervals examined, but one its regulatory proteins, p35, was robustly upregulated. Despite this change in p35, its truncated product, p25 was not reproducibly detected.

When tested in hippocampal extracts from wt and knockout mice, each of the stress-responsive kinase forms or regulators also exhibited modulation as a function of CRF-R status that mirrored some or all of effects of genotype on restraint-induced tau-P. The activated ($pY^{216}$) form of GSK-3β, implicated in phosphorylating tau at $S^{199}$, $S^{212}$, $T^{231}$ and PHF-1 sites, was most similar in that the stress-induced increment seen in wt mice was not evident in CRF-R1−/− animals, and exaggerated in CRF-R2−/− mice. Phosphorylation responses of both JNK isoforms were also significantly greater in CRF-R2 knockouts than in wt controls ($P<0.05$). These kinases also exhibited pronounced elevations in basal phosphorylation in CRF-R1-deficient mice, whose magnitude rivaled or exceeded stress-induced levels in wt mice. This may relate to the elevated tau-P levels seen under this condition at the AT8 and PHF-1 sites, though less marked elevations of phosphorylated GSK-3β and ERK2, and of p35 levels, in unstressed CRF-R1−/− mice may also contribute in this regard. Overall, these results identify several tau kinases as potential effectors of CRF-R-dependent effects of acute emotional stress on tau-P.

Example 7

Tau Phosphorylation in Response to Repeated Stress

Because past and present data characterize acute stress-induced tau-P as a transient phenomenon, its relevance to neuropathology may be questioned. Data from animal models and the AD brain have demonstrated that NFTs and other manifestation of tau pathology are dependent on aberrantly phosphorylated tau being sequestered into insoluble cellular fractions (Iqbal et al., 1994). Therefore, sequential fractionation was used in the absence (RAB buffer; see methods) and then in the presence of detergents (RIPA buffer) to compare the persistence and solubility of phosphorylated tau in animals subjected to acute versus repeated (14 consecutive daily exposures) restraint stress (FIG. 7). Groups of mice in each condition were sacrificed 20 min or 24 hr after their final or only stress episode. Results from the acute stress condition replicated findings detailed above in showing increased phosphorylation at the AT8 and PHF-1 sites 20 min post-stress. At 24 hr post-stress, relative levels of tau-P were indistinguishable from unstressed animals (lane 3). In terms of solubility, phosphorylated tau induced by acute stress was detected only in the soluble fraction; that is, no additional signal was evident upon further extraction with detergent (lanes 6-8). In contrast, under repeated stress conditions, comparably elevated AT8 and PHF-1 signal were present in soluble fractions at both 20 min and 24 hr after the final restraint episode. In addition, extraction of detergent-soluble proteins (RIPA) revealed significant occurrence of phosphorylated tau at both time points (lanes 9-10). These results suggest that repeated stress leads to chronic elevations in phosphorylated tau, and a shift in its disposition toward more insoluble, and potentially pathogenic, forms.

Example 8

Phosphatase Involvement in Restraint-Induced Tau Phosphorylation

In addition to changes in tau kinases, alterations in tau phosphatase activity has been implicated as contributing to stress-induced tau-P (Planel et al., 2001, 2004, 2007). To determine whether similar changes may be associated with acute or repeated restraint stress, the same extracts used in the preceding analysis (FIG. 7A-B), were studied for alterations in the catalytic subunit of the dominant tau phosphatase, PP2A (PP2A-c). No evidence of PP2A-c within detergent-soluble RIPA fractions under was found under any experimental condition. In soluble RAB fractions, relative levels of PP2A-c from hippocampi of acute stressed mice did not differ reliably from those of controls (lanes 1-3), but were significantly elevated at both 20 min ($P<0.001$) and 24 hr after repeated restraint ($P<0.01$; lanes 4-5; see FIG. 7C).

These findings identify PP2A as a potential contributor to alterations in tau-P, at least under repeated stress conditions.

Example 9

Stressor Specificity of CRFR Involvement

The studies relating CRFR modulation of tau-P in the hippocampus under acute stress conditions were carried out using a prototypic "emotional" stressor, physical restraint. Established animal models of anxiety (elevated plus maze exposure), fear (open field exposure, conditioned fear) and social stress (social defeat, isolation), share in common with restraint such key features as a capacity to engage a stereotyped set of interconnected cell groups in the limbic forebrain, including hippocampus (Duncan et al., 1996; Campeau et al., 1997; Martinez et al., 2002). "Emotional" is one of two major categories of stressors, and is distinguished from the other, "physiological" type by the nature of the sensory input that registers the challenge, the extent to which they invoke affective responses, and the global pattern of activational responses they induce within the brain (Sawchenko et al., 1996; Herman and Cullinan, 1997; Sawchenko et al., 2000; Dayas et al., 2001). To determine whether differential CRFR dependence extends to categorically distinct stressors, an immune challenge induced by bacterial lipopolysaccharide (LPS), which serves as an animal model of systemic infection, was applied to subject mice and was examined for its effect on tauopathy in subject mice. The LPS induced stress is a well-characterized physiological stress (Turnbull et al., 1999).

Initial time course studies using the LPS induced challenge has shown robust increases in hippocampal tau-P, peaking at 60-90 min post-injection (FIG. 9A). Assessments of the genotype dependence of this effect yielded results quite distinct from those obtained with in the restraint model (FIG. 9B). Thus, acute LPS treatment resulted in enhanced phosphorylation at the PHF-1 site in wt, single and double CRFR knockouts with only subtle variation, which included a tendency for tau-P responses to be enhanced in CRFR1-deficient mice. Phosphorylation responses at the AT8 epitope (assessed in the same extracts) were quite variable in CRFR2 and double knockout mice, with two of three animals in each group displaying tau-P levels at or near control values. While the basis for this variability is uncertain, these results indicate that neither the strong and consistent CRFR1 dependence of restraint-induced tau-P that we have describe, nor the tendency of CRFR2 deficiency to exaggerated these responses, generalize to the LPS model. This raises the intriguing possibility that CRFR involvement may be limited to emotional stressors.

Example 10

Phenotypic Characterization Using a CRF-R1Expressing Transgenic Mouse Line

Figure 10:
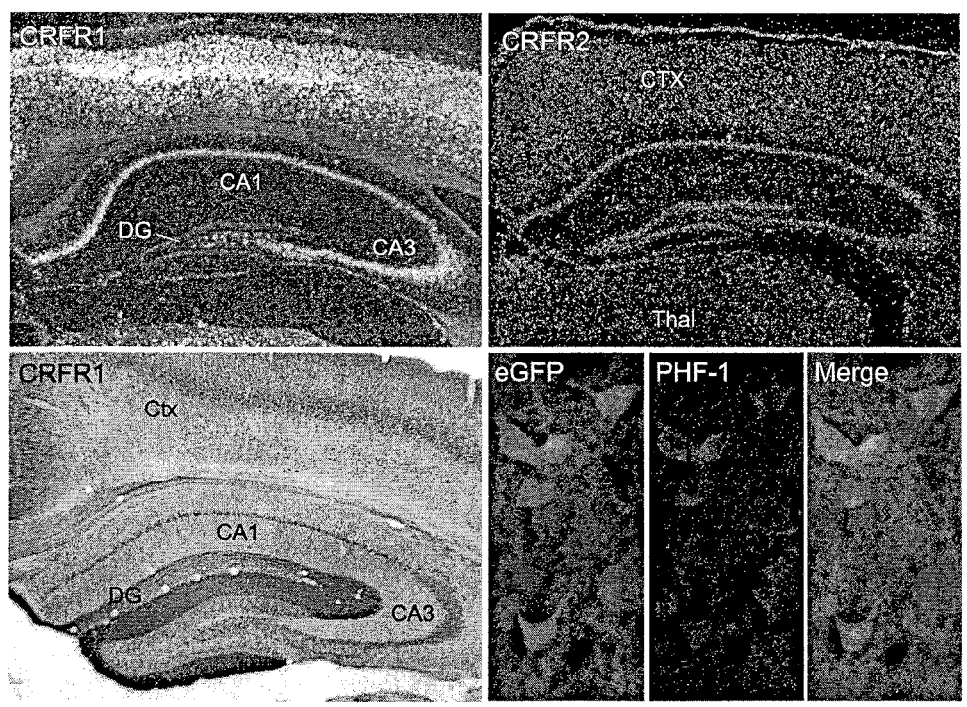
FIG. 10: Hippocampal CRFR mRNA and transgenic eGFP expression. Top: CRFR1 (left) and CRFR2 (right) in hippocampus by in situ hybridization. CRFR1 transcripts are expressed in Ammon's horn (CA1, CA3) and the hilar region of the dentate gyms, while CRFR2 is weakly expressed throughout the principal cell layers. Bottom: Immuno-peroxidase staining for eGFP in a BAC transgenic mouse expressing eGFP under control of the CRFR1 promoter (left). The cellular distribution of labeling in hippocampus and cortex is similar to that of CRFR1 mRNA. Axonal projections of CRFR1 neurons (bands of punctate labeling) are also prominently and differentially labeled in the transgenic mouse. Color images at the right are of neurons in the dentate hilus of an acutely restrained CRFR1-eGFP mouse co-stained for eGFP and PHF-1 (merged channel at far right). Substantial overlap localizes stress-induced tau-P to CRFR1-expressing hilar neurons.

An initial step in unraveling the circuitry that provides for modulation of stress-induced tau-P by CRF signaling pathways will require identifying CRFR-expressing hippocampal neurons that manifest stress-induced tau-P. To facilitate this analysis, the inventors have generated and validated a transgenic mouse line that reports expression of CRFR1. The enhanced green fluorescent protein (eGFP) reporter construct is based on a bacterial artificial chromosome (BAC) that contains large amounts of sequence surrounding CRFR1 such that expression of eGFP is controlled by promoter and enhancer sequences that regulate endogenous receptor expression. Reporter expression in this mouse line marks the CRFR1 phenotype with high sensitivity, accuracy and cellular resolution, as determined by direct comparisons with CRFR1 mRNA expression (FIG. 10). As with other transgenic lines generated using this approach, normal function of the receptor is not affected (Heintz, 2001).

CRFR1-eGFP mice were exposed to acute or repeated restraint and was examined for dual localization of eGFP and PHF-1 immunoreactivity. Confocal microscopic analysis of doubly stained material reveals near complete overlap in cellular expression of stress-induced PHF-1 with CRFR1-driven eGFP in the hilar region of the dentate gyms, and substantial colocalization in pyramidal neurons of Ammon's horn. It is of interest that labeling in the transgenic extends to dendritic and axonal process of CRFR1-expressing neurons, with prominent terminal-like labeling seen in some cases (FIG. 10). While it cannot be assumed that the latter represent sites of presynaptic receptor expression, it is consistent with this possibility. Overall, the CRFR1-eGFP mouse will provide a sensitive and high-resolution tool of characterizing sites of CRFR1 expression, which partially overcomes the lack of specific CRFR antisera.

Example 11

Characterization of Insoluble Tau Aggregates

Figure 11:
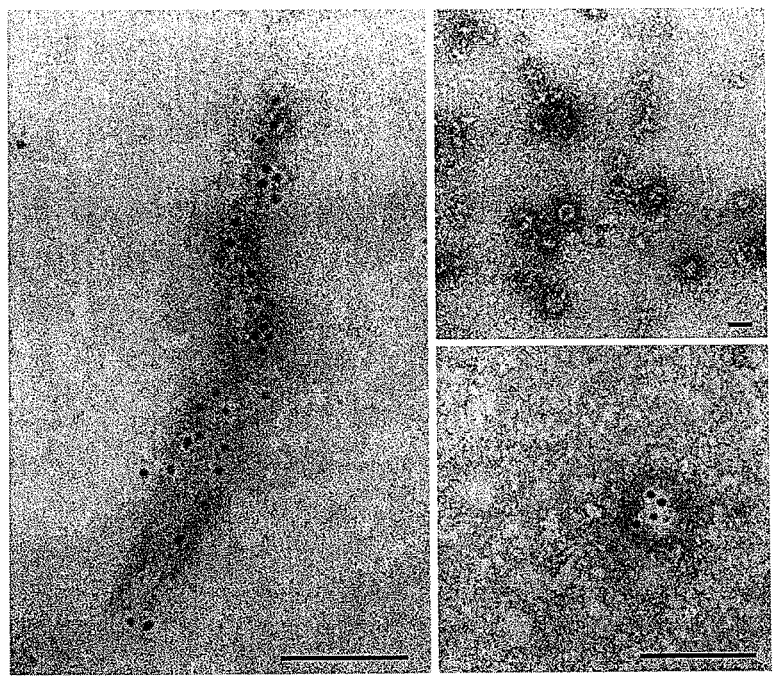
FIG. 11: Immunoelectron microscopy of tau filaments and aggregates. Left: Paired-helical filament from an AD brain (Braak stage VI) negatively stained and immunogold labeled (black dots) for phospho-tau using the PHF-1 antibody. Right: Image of (non-immunolabeled) RIPA extract from a mouse subject to 14 d repeated restraint stress (top) shows negatively stained round/globular aggregates (40-100 nm diameter) that were never seen in unstressed, acutely stressed, or soluble extracts of repeatedly stressed mice. These, too, can be decorated by PHF-1-immunogold labeling (bottom), confirming the presence of phospho-tau. Scale bars=100 nm.

NFTs consisting of PHFs are a diagnostic feature of AD. PHFs can be imaged by transmission electron microscopy of heavy metal-stained ultrathin sections or extracts of the AD brain, where they comprise ~10-20 nm diameter cylindrical filaments with helical period of ~80 nm (Greenberg and Davies, 1990). They can be decorated by immunogold labeling to localize antibodies, such as PHF-1, to affirm the presence of phosphorylated tau species. The inventors have validated procedures for labeling and imaging PHFs in extracts from AD brains (FIG. 11).

In addition, similar methods were used to image RIPA extracts of hippocampi from mice subjected to the 14 d repeated restraint stress paradigm described above. The RIPA extracts contain the bulk of dispersed PHFs in the AD brain (Iqbal et al., 1984; Rubenstein et al., 1986). In this material, nothing resembling PHF-like filaments was detected, as it was expected to. However, the samples were observed containing numerous structures of consistent form, rounded globular aggregates 40-100 nm in diameter (mean=69 nm), that label positively and specifically for phosphorylated tau (PHF-1). The size and shape of these structures are highly reminiscent of those of aggregates assembled from N-terminally truncated human tau under cell-free conditions (King et al., 2000). This may suggest that phosphorylated tau species accumulating in the preparations are truncated or cleaved as a result of stress, though prior Western analyses on the samples provided little evidence of this. While tau truncated in this way cannot form filaments in cell-free systems, it did so in vivo, and has been implicated in NFT formation and neurodegeneration (Mailliot et al., 1998; Rohn et al., 2002). Although requiring confirmation and extension, these findings may represent the first evidence of pre-pathologic tau aggregates, in vivo. That the tau aggregates can occur after a limited duration of intermittent exposure to a moderate stressor is striking, and may indicate that stress alone is capable of initiating pathogenic changes in tau.

Example 12

Repeated Stress Induced Tau-Phosphorylation Effects are CRFR-Dependent

The CRFR status dependency of accumulation and altered solubility of phosphorylated tau species was examined in repeatedly stressed mice. This experiment is an extension of the repeated stress study described above in wt, CRFR1−/−, CRFR2−/ and double knockout mice. The experiment yielded a 2×3×4×2 design with two stress conditions (acute, repeated), three post-stress time points for each (0, 20 min, 24 hr), four genotypes and two extraction conditions (soluble, insoluble) for a total of 48 groups. Data for one key tau epitope (PHF-1) are shown in FIG. 12A. With respect to genotype, results in wt mice fully support the analysis above, a cumulative effect of repeated stress on tau-P at the PHF-1 site (compare acute vs repeated 24 hr lanes). In addition, the results obtained to date extend the inventors' basic findings regarding CRFR-dependence to the repeated stress condition. Thus, under no condition did the response of CRFR1-deficient mice exceed that of unstressed wt controls, while responses of CRFR2 mutants were at least comparable, and tended to exceed, those of genetically intact animals. In addition, mice deficient in both genes fail to respond to acute or repeated stress in a manner similar to CRFR1 mutants. With respect to the solubility of PHF-1-phosphorylated tau under repeated stress conditions, the data shown in FIG. 12B indicate that chronic effects of stress (i.e., 24 hr after the final exposure) are seen in both the soluble and insoluble fractions of wt mice, that these effects tend to be exaggerated in R2 mutants, and that stress-induced tau-P at the PHF-1 site is completely lacking in CRFR1 and double knockout mice.

Collectively, these findings suggest that the genotype-dependence observed in acutely restrained mice extends to repeated stress effects on tau-P and solubility. Data from double knockout animals would indicate that CRFR2-mediated effects on these parameters are CRFR1-dependent, and likely lie upstream of them in the associated circuitry. The inventors will further exploit the material generated in this study to provide a more complete characterization of repeated stress effects on tau-P and solubility, and extend the analysis to amyloid processing and dynamics.

Example 13

Effects of CRF-R1 Antagonist on the Development of Amyloid Pathology in a Mouse Model of AD Insoluble plaques consisting of Aβ, which is derived from sequential proteolytic processing of APP, is the second defining hallmark of AD neuropathology. Aβ is generated by sequential proteolysis of APP by β secretase and presenilin-dependent γ secretase. Two lines of evidence warranted extension of this study to include analyses of APP processing in repeated stress paradigms. First, while both isoforms of GSK-3 can phosphorylate tau, GSK-3β is heavily studied in tau pathology because of its localization as a component of NFTs and its propensity to induce tangle pathology (Rankin et al., 2007). On the other hand, GSK-3α has been found to be required for maximal APP processing and Aβ production (Phiel et al., 2003). The analysis of kinase modulation indicated that GSK-3α is as potently activated by acute restraint as GSK-3β, and that the response of both isoforms shows a similar and differential dependence on CRFR status. Second, a recent report documented that restraint stress, or central CRF administration, can increase interstitial fluid levels of A> albeit in APP transgenic mice (Kang et al., 2007).

Figure 13:
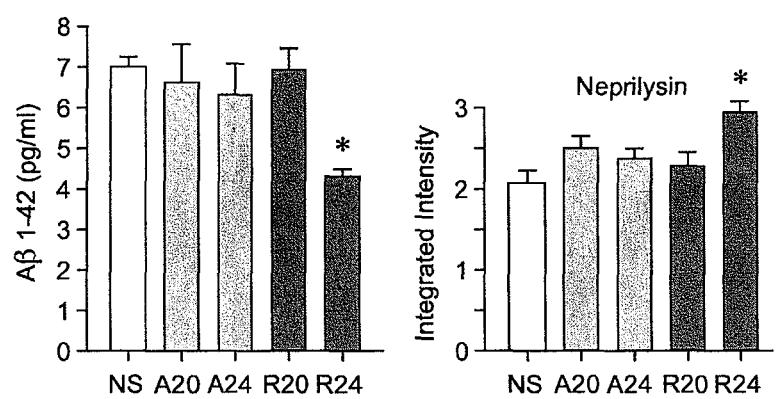
FIG. 13: Modulation of Amyloid beta (Aβ) by repeated stress. The bar graphs show the mean levels of Aβ42 (ELISA) and the Aβ-degrading enzyme, neprilysin (Western analysis), in RIPA hippocampal extracts of mice sacrificed at 20 min (20) or 24 hr (24) after their only (acute stress; A) or final of 14 consecutive daily (repeated stress; R) exposure(s) to restraint stress. Acute stress did not affect either measure. Subtle but significant reductions in levels of Aβ42, and increases in neprilysin levels, are seen 24 hr after the last exposure in repeated stress, relative to unstressed controls. *, $P<0.05$.

Accordingly, alterations in amyloid processing affected by emotional stress were studied. In RIPA extracts (Aβ was not detected in formic acid fractions), no significant change in Aβ42 levels was observed. The Aβ42 levels were assessed by sandwich ELISA, at 20 min after either acute or repeated stress exposure. However, levels of Aβ42 were observed decreasing significantly 24 hr after the last of the repeated stress exposures (P=0.02; FIG. 13). Western analyses revealed a concomitant increase in levels of neprilysin (an Aβ-degrading enzyme), relative to unstressed controls (P<0.01). APP levels (assessed using antibody 22C11) did not vary reliably across experimental conditions (data not shown). This pattern of results is suggestive of increased amyloid clearance under repeated stress conditions, and, while subtle, do provide an initial indication that stress can impact Aβ and related enzymes in hippocampus.

A transgenic mouse model of AD was picked and used to directly assess the role of stress and perturbations in CRF signaling in AD pathogenesis. There are a number of such mouse lines, which involve transgenic expression of mutant forms of human amyloid precursor protein (APP), presenilin and/or tau, singly or in combination (reviewed in (Spires and Hyman, 2005; Gotz et al., 2007)). We chose one that overexpresses mutant human APP and presenilin-1 (PS/APP model; Jankowsky et al., 2001), which show predominantly amyloid pathology in cortex and hippocampus beginning at 3-4 months of age, with 6 months considered the time of onset of pathology (Jankowsy et al., 2004). Alterations in tau are subtler, slower to develop, and occur in association with amyloid plaques. NFTs have not been reported in this line. Only in transgenic models expressing mutant tau species has tangle formation been found to occur (Spires and Hyman, 2005; Gotz et al., 2007). The PS/APP line is ideally suited to the presented study as it presents an AD-like amyloid phenotype in hippocampus and cortex, while allowing the effects of stress experience on tau to be isolated.

Separate groups of PS/APP mice were or were not subjected to two 14-day exposures to a chronic variable stress paradigm (CVS; see Example 1) at beginning of their fourth and fifth months of life in the presence or absence of concurrent treatment with the CRFR1 antagonist, antalarmin (40 mg/kg/d; ip) or vehicle. The choice of CVS as a stress regimen was based on the considerations that it was quite potent, resistant to habituation, more naturalistic (Marin et al., 2007) and it afforded the opportunity for pharmacologic intervention. All animals were sacrificed at the end of the fifth month of life, shortly after the time at which amyloid plaques begin to appear in this line.

Figure 14:
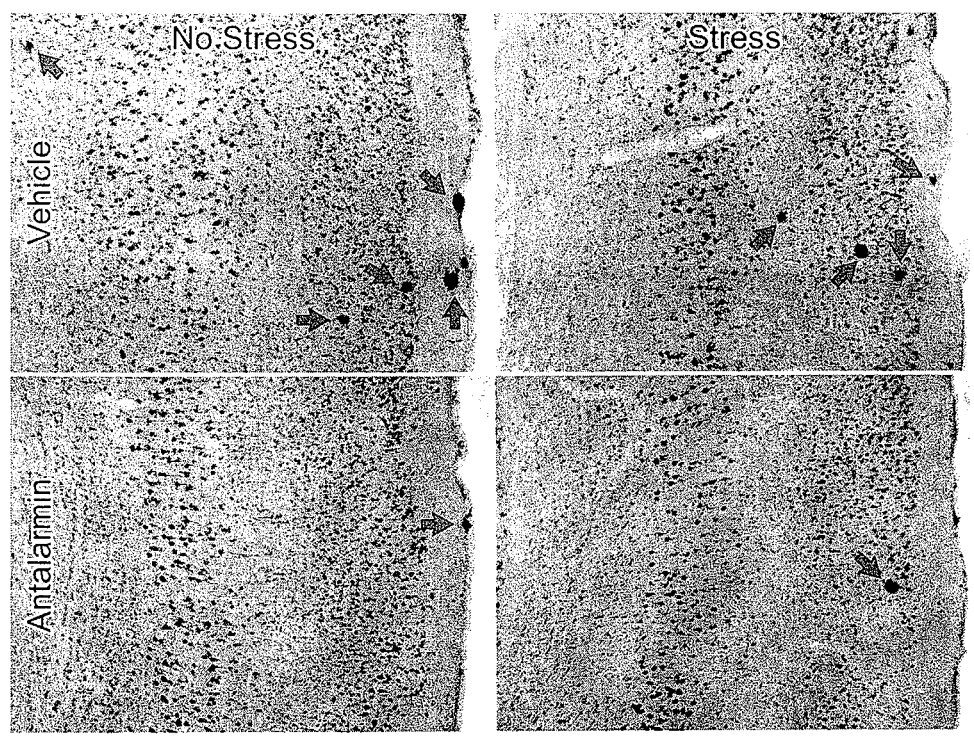
FIG. 14: Stress and CRFR1 antagonist effects in a mouse AD model. Groups of PS/APP mice were subjected to two 14-day exposures to chronic variable stress at beginning of the fourth and fifth months of age in the presence or absence of concurrent treatment with the CRFR1 antagonist, antalarmin (40 mg/kg/d; ip) or vehicle. Parallel groups without exposure to stress were also administered with antalarmin (40 mg/kg/d; ip) or vehicle as control groups. All animals were sacrificed at the end of the fifth month of life, shortly after the time at which amyloid plaques begin to appear in this transgenic mouse line. Comparable fields of the cerebral cortex of the PS/APP transgenic mouse model of AD were prepared and stained with an antiserum directed against the N-terminus of human APP. The density of plaques (arrows)

Immunohistochemical localization of phosphorylated tau (PHF-1) revealed only subtle variations in staining as a function of treatment status. There was no evidence of tau pathology (tangle formation), nor was it expected to develop in animals at this early stage of disease progression. Examination of plaque formation by immunohistochemical (using antibody clone 6E10; specific to the N-terminus of human Aβ) or histochemical (thioflavin S) methods did reveal a marked effect of these manipulations (FIG. 14). While CVS exposure exerted no major effect on the density of plaques in cortex and hippocampus, antalarmin treatment significantly reduced in this measure in both stressed (2.49/mm$^2$) and unstressed (1.15/mm$^2$) groups, relative to unstressed vehicle-treated controls (9.38/mm$^2$). Thus, exposure for a limited time to the CRFR1 antagonist blocked or delayed the development of amyloid pathology in this mouse AD model.

While it remains to be determined whether this effect will maintain in older animals, and whether drug and/or stress exposure will affect tau pathology, the results provide an additional endorsement for considering CRFR1 as a therapeutic target in AD.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 5,109,111
U.S. Pat. No. 5,245,009
U.S. Pat. No. 5,510,458
U.S. Pat. No. 5,777,073
U.S. Pat. No. 5,874,227
U.S. Pat. No. 6,147,275
U.S. Pat. No. 6,323,312
U.S. Pat. No. 6,353,152
U.S. Pat. No. 6,569,620
U.S. Pat. No. 6,716,580
U.S. Pat. No. 6,787,140
U.S. Pat. No. 6,838,274
U.S. Pat. No. 6,953,838
U.S. Pat. No. 7,125,990
U.S. Publn. 20030186867
Alonso et al., *Nat. Med.*, 2:783-787, 1996.
Arborelius et al., *J. Endocrinol.*, 160:1-12, 1999.
Arendt et al., *J. Neurosci.*, 23:6972-6981, 2003.
Arriagada et al., *Neurology*, 42:631-639, 1992.
Arzt and Holsboer, *Trends Pharmacol. Sci.*, 27:531-538, 2006.
Atzori et al., *J. Neuropathol. Exp. Neurol.*, 60:1190-1197, 2001.
Baharians and Schonthal, *J. Biol. Chem.*, 273:19019-19024, 1998.
Bale et al., *Nat. Genet.*, 24:410-414, 2000.
Bale and Vale, *J. Neurosci.*, 23:5295-5301, 2003.
Bale and Vale, *Annu. Rev. Pharmacol. Toxicol.*, 44:525-557, 2004.
Baram et al., *Ann. NY Acad. Sci.*, 814:252-265, 1997.
Bayatti and Behl, *Ageing Res. Rev.*, 4:258-270, 2005.
Behan et al., *Nature*, 378:284-287, 1995.
Bittencourt and Sawchenko, *J. Neurosci.*, 20:1142-1156, 2000.
Boekhoorn et al., *J. Neurosci.*, 26:3514-3523, 2006.
Braak and Braak, *Acta Neuropathol. (Berl)*, 82:239-259, 1991.
Bramblett et al., *Neuron.*, 10:1089-1099, 1993.
Campeau et al., *Neuroscience*, 78:1087-1104, 1997.
Chadwick et al., In: *Corticotropin-releasing factor*, Chichester (Ed.), NY, Wiley, 1993.
Chen & Grigoriadis, *Drug Dev. Res.*, 65(4):216-226, 2005
Chen et al., *Neuroscience*, 126:533-540, 2004.
Clement et al., *J. Pharmacol. Methods*, 21:129-140, 1989.
Cohen and Frame, *Nat. Rev. Mol. Cell. Biol.*, 2:769-776, 2001.
Cole et al., *J. Biol. Chem.*, 279:50176-50180, 2004.
Coste et al., *Nat. Genet.*, 24:403-409, 2000.
Davis et al., *Arch. Gen. Psychiatry*, 56:981-987, 1999.
Dayas et al., *Eur. J. Neurosci.*, 14:1143-1152, 2001.
De La Garza, *Clin. Pharmacol.*, 68(7):1365-1372, 2003
De Souza et al., *Nature*, 319:593-595, 1986.
Drewes, *Trends Biochem. Sci.*, 29:548-555, 2004.
Drewes et al., *Embo. J.*, 11:2131-2138, 1992.
Duncan et al., *Brain Res.*, 713:79-91, 1996.
Egleton & Davis, *NeuroRx.*, 2(1):44-53, 2005.
Feng et al., *Neurosci. Lett.*, 388:13-16, 2005.
Fingl et al., In: *The Pharmacological Basis of Therapeutics*, 1:1, 1975.
Freireich et al., *Cancer Chemother. Reports*, 50:219-244, 1966.
Fuchs et al., *Front Biosci.*, 11:2746-2758, 2006.
Gerhlert et al., *J. Neurosci.*, 27(10):2718-2726, 2007.
Gilligan et al., *J. Med. Chem.*, 43(9):1641-1660, 2000.
Goedert et al., *Neuron.*, 3:519-526, 1989.
Gomez-Isla et al., *Ann. Neurol.*, 41:17-24, 1997.
Grammatopoulos and Chrousos, *Trends Endocrinol. Metab.*, 13:436-444, 2002.
Green et al., *J. Neurosci.*, 26:9047-9056, 2006.
Gustke et al., *FEBS Lett.*, 307:199-205, 1992.
Hartig et al., *Eur. J. Neurosci.*, 25:69-80, 2007.
Hartigan et al., *Biochem. Biophys. Res. Commun.*, 284:485-489, 2001.
Heinrichs et al., *Neuropsychopharmacology* 27(2):194-202, 2002.
Herman and Cullinan, *Trends Neurosci.*, 20:78-84, 1997.
Higuchi et al., *Neuron.*, 35:433-446, 2002.
Hillhouse and Grammatopoulos, *Endocr. Rev.*, 27:260-286, 2006.
Holmes et al., *Trends Pharm. Sci.*, 24(11):580-588, 2003.
Hutton et al., *Nature*, 393:702-705, 1998.
Ikeda et al., *FEBS Lett.*, 581:891-897, 2007.
Iqbal et al., *Mol. Neurobiol.*, 9:119-123, 1994.
Iqbal et al., *Acta Neuropathol. (Berl)*, 62:167-177, 1984.
Jankowsky et al., Biomol Eng, 17:157-165, 2001
Jankowsky et al., Hum Mol Genet., 13:159-70, 2004
Jeong et al., *Faseb J.*, 20:729-731, 2006.
Kampers et al., *FEBS Lett.*, 451:39-44, 1999.
Keller et al., *Drug Metab. Dispos.*, 30(2):173-176, 2002.
Kishimoto et al., *Nat. Genet.*, 24:415-419, 2000.
Kopke et al., *J. Biol. Chem.*, 268:24374-24384, 1993.
Korneyev et al., *Neurosci. Lett.*, 191:19-22, 1995.
Korneyev, *Neurochem. Res.*, 23:1539-1543, 1998.
Kosik et al., *Neuron.*, 2:1389-1397, 1989.
Kraemer et al., *Proc. Natl. Acad. Sci. USA*, 100:9980-9985, 2003.
Kyte and Doolittle, *J. Mol. Biol.*, 157(1):105-132, 1982.
Lee et al., *J. Protein Chem.*, 17:15-27, 1998.
Li et al., *CNS Drug Rev.*, 11(1):21-52, 2005
Liu et al., *J. Neurochem.*, 87:1333-1344, 2003.
Mahmood et al., *J. Clin. Pharmacol.*, 43:692-697, 2003.
Martinez et al., *Stress*, 5:3-13, 2002.
Mazur et al., *Peptides*, 26(5):887-891, 2005.
McCarthy et al., *Curr. Pharm. Des.*, 5(5):289-315, 1999.
Meijer et al., *Lab. Anim.*, 40:382-391, 2006.

Million et al., *Brain Res.*, 985(1):32-42, 2003.
Okawa et al., *FEBS Lett.*, 535:183-189, 2003.
Olivier, *NeuroRx.*, 2(1):108-119, 2005.
Papasozomenos, *J. Neurochem.*, 66:1140-1149, 1996.
Patrick et al., *Nature*, 402:615-622, 1999.
PCT Appln. WO 2005/014041
Pedersen et al., *J. Neurosci.*, 22:404-412, 2002.
Pernar et al., *J. Neurosci.*, 24:1305-1311, 2004.
Planel et al., *J. Neurosci.*, 24:2401-2411, 2004.
Planel et al., *J. Neurosci.*, 27:3090-3097, 2007.
Planel et al., *J. Biol. Chem.*, 276:34298-34306, 2001.
Poorkaj et al., *Ann. Neurol.*, 43:815-825, 1998.
Powers et al., *Synapse*, 1:405-410, 1987.
Raadsheer et al., *Am. J. Psychiatry*, 152:1372-1376, 1995.
Rehman, *Curr. Opin. Investig. Drugs*, 3:1637-1642, 2002.
Remington's Pharmaceutical Sciences, 18th Ed. Mack Printing Company, 1990
Rijkers et al., *Bioorg. Med. Chem.*, 12(19):5099-5106, 2004.
Rivier et al., *J. Med. Chem.*, 45:4737-4747, 2002.
Rubenstein et al., *Brain Res.*, 372:80-88, 1986.
Sapolsky et al., *J. Neurosci.*, 5:1222-1227, 1985.
Sapolsky et al., *Endocr. Rev.*, 7:284-301, 1986.
Sawchenko et al., *Prog. Brain Res.*, 107:201-222, 1996.
Sawchenko et al., *Prog. Brain Res.*, 122:61-78, 2000.
Schnyder & Huwyler, *NeuroRx.*, 2(1):99-107, 2005.
Sengupta et al., *Arch. Biochem. Biophys.*, 357:299-309, 1998.
Shu et al., *J. Chem. Neuroanat.*, 1:147-163, 1988.
Smith et al., *Neuron.*, 20:1093-1102, 1998.
Spencer & Verma, *Proc. Natl. Acad. Sci. USA*, 104(18):7594-7599, 2007.
Spillantini et al., *Proc. Natl. Acad. Sci. USA*, 95:7737-7741, 1998.
Stamer et al., *J. Cell Biol.*, 156:1051-1063, 2002.
Swaab et al., *Ageing Res. Rev.*, 4:141-194, 2005.
Tache et al., *British J. Pharm.*, 141:1321-1330, 2004)
Timpl et al., *Nat. Genet.*, 19:162-166, 1998.
Turek and Ryabinin, *Brain Res.*, 1063:132-139, 2005.
Turnbull et al., *Physiol Rev.* 79:1-71, 1999
Vale et al., *Science*, 213:1394-1397, 1981.
Van Pett et al., *J. Comp. Neurol.*, 428:191-212, 2000.
Watanabe et al. *Risk Analysis*, 12:301-310, 1992.
Watts, *Front Neuroendocrinol.*, 17:281-326, 1996.
Webster et al., *Endocrinology*, 137:5747-5750, 1996.
Wilson et al., *Neurology*, 61:1479-1485, 2003.
Yanagisawa et al., *FEBS Lett.*, 461:329-333, 1999.
Yoshida et al., *J. Neural. Transm.*, 113:1803-1814, 2006.
Zorrilla et al., *Trends Pharmacol. Sci.*, 24(8):421-427, 2003.

The invention claimed is:

1. A method for treating a subject afflicted with stress-induced Alzheimer's disease, the method comprising:
   (a) determining that a subject is afflicted with a stress-induced Alzheimer's disease by assessment of one or more of a genetic predisposition, age or a risk factor selected from declining cognitive function, and declining memory function; and
   (b) reducing tau phosphorylation in the subject by administering to the subject an amount of a CRF-R1 selective antagonist that binds to and inhibits CRF-R1 and is effective to reduce tau phosphorylation in the subject.

2. The method of claim 1, wherein the CRF-R1 selective antagonist has between about 10 and about 100, 1000, or 10,000 fold more antagonist activity of CRF-R1 than CRF-R2.

3. The method of claim 1, wherein the CRF-R1 selective antagonist has no CRF-R2 antagonist activity.

4. The method of claim 1, wherein the CRF-R1 selective antagonist is administered to the subject intranasally.

5. The method of claim 1, wherein the CRF-R1 selective antagonist is NBI 27914.

* * * * *

UNITED STATES PATENT AND TRADEMARK OFFICE
CERTIFICATE OF CORRECTION

PATENT NO. : 9,555,032 B2  
APPLICATION NO. : 12/663805  
DATED : January 31, 2017  
INVENTOR(S) : Robert A. Rissman et al.

It is certified that error appears in the above-identified patent and that said Letters Patent is hereby corrected as shown below:

In the Claims

In Claim 1, Column 39, Lines 25-26, delete "with a stress-induced" and insert --with stressed-induced-- therefor.

Signed and Sealed this  
Second Day of May, 2017

Michelle K. Lee  
*Director of the United States Patent and Trademark Office*